(12) United States Patent
McVey

(10) Patent No.: US 6,875,399 B2
(45) Date of Patent: Apr. 5, 2005

(54) NON-DISPERSIVE MID-INFRARED SENSOR FOR VAPORIZED HYDROGEN PEROXIDE

(75) Inventor: Iain F. McVey, Lakewood, OH (US)

(73) Assignee: Steris Inc., Temecula, CA (US)

( * ) Notice: Subject to any disclaimer, the term of this patent is extended or adjusted under 35 U.S.C. 154(b) by 200 days.

(21) Appl. No.: 10/142,678

(22) Filed: May 10, 2002

(65) Prior Publication Data

US 2002/0168289 A1 Nov. 14, 2002

Related U.S. Application Data

(60) Provisional application No. 60/290,599, filed on May 11, 2001.

(51) Int. Cl.[7] .................................................. A61L 2/00
(52) U.S. Cl. ...................... 422/3; 250/339.13; 250/343; 422/4; 422/28; 422/105; 422/108; 422/110; 422/111
(58) Field of Search .......................... 422/3, 4, 28, 105, 422/108, 110, 111; 250/339.13, 343

(56) References Cited

U.S. PATENT DOCUMENTS

| | | |
|---|---|---|
| 3,735,127 A | 5/1973 | Astheimer |
| 4,182,743 A | 1/1980 | Rainer et al. |
| 4,525,265 A | 6/1985 | Abe et al. |
| 4,843,867 A | 7/1989 | Cummings |
| 4,863,688 A | 9/1989 | Schmidt et al. |
| 4,891,518 A | 1/1990 | Day |
| 4,914,719 A | 4/1990 | Conlon et al. |
| 4,956,145 A | 9/1990 | Cummings et al. |
| 5,173,258 A | 12/1992 | Childers |
| 5,320,725 A | 6/1994 | Gregg et al. |
| 5,394,730 A | 3/1995 | Crozier et al. |
| 5,445,792 A | 8/1995 | Rickloff et al. |
| 5,451,787 A | 9/1995 | Taylor |
| 5,508,009 A | 4/1996 | Rickloff et al. |
| 5,600,142 A | 2/1997 | Van Den Berg et al. |
| 5,608,156 A | 3/1997 | Ando et al. |
| 5,723,864 A | 3/1998 | Atkinson et al. |
| 5,847,392 A | 12/1998 | Van Den Berg et al. |
| 5,847,393 A | 12/1998 | Van Den Berg et al. |
| 5,872,359 A | 2/1999 | Stewart et al. |
| 5,886,348 A | 3/1999 | Lessure et al. ........ 250/339.13 |
| 5,892,229 A | 4/1999 | Crozier et al. ......... 250/339.13 |
| 5,906,794 A | 5/1999 | Childers |
| 5,942,754 A * | 8/1999 | Yamaguchi et al. ... 250/339.12 |
| 5,976,466 A | 11/1999 | Ratner et al. |
| 6,077,480 A | 6/2000 | Edwards et al. |
| 6,129,831 A | 10/2000 | Temmerman et al. |

FOREIGN PATENT DOCUMENTS

EP        384 535        8/1990

OTHER PUBLICATIONS

G. Echle, H. Oelhaf and A. Wegner, "On the Potential of I.R. Limb Emission Spectroscopy for the Measurement of the Stratospheric Composition," *J. Quant. Spectrosc. Radiat. Transfer.* vol. 52, No. 3/4, pp. 253–265, (1994).

* cited by examiner

*Primary Examiner*—Krisanne Jastrzab
(74) *Attorney, Agent, or Firm*—Fay, Sharpe, Fagan, Minnich & McKee, LLP

(57) ABSTRACT

A sterilization system (14) includes a sensor (10) for detection of a component, such as hydrogen peroxide vapor, in a multi-component vapor, such as a mixture of vapor hydrogen peroxide and water supplied to a chamber (12) of the system. The sensor preferably uses a wavelength range in which hydrogen peroxide strongly absorbs but other components of the vapor, such as water, do not. A suitable wavelength for detection of hydrogen peroxide is from about 7500 to about 8400 nm, since there is little absorption by water in this range. This avoids the need to use complex subtraction procedures normally used to remove the contribution of water from detected absorbance measurements. A control system (16, 30) controls operating conditions of the sterilization system, such as a heater (82), pressure release valves (74), vaporization rate of hydrogen peroxide by a vaporizer (22), and the like to maintain optimum sterilization conditions within the chamber.

25 Claims, 10 Drawing Sheets

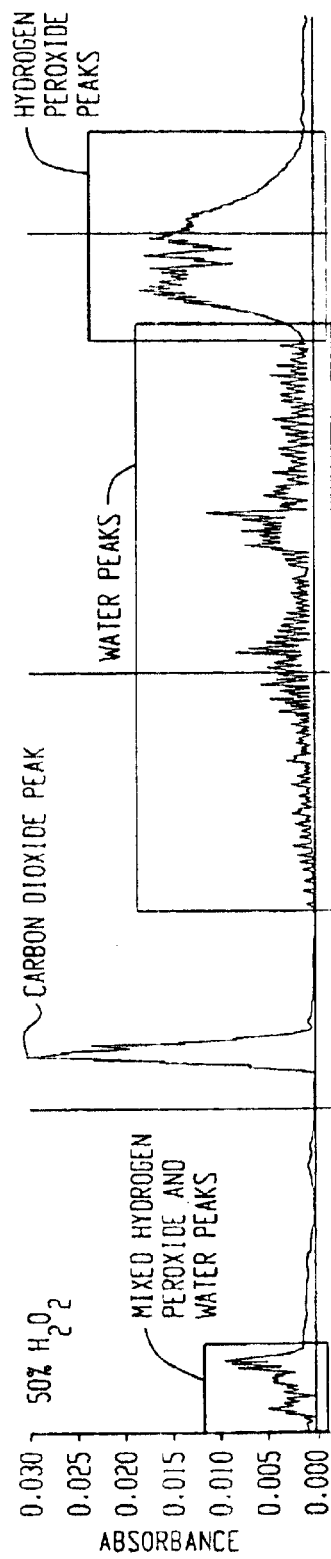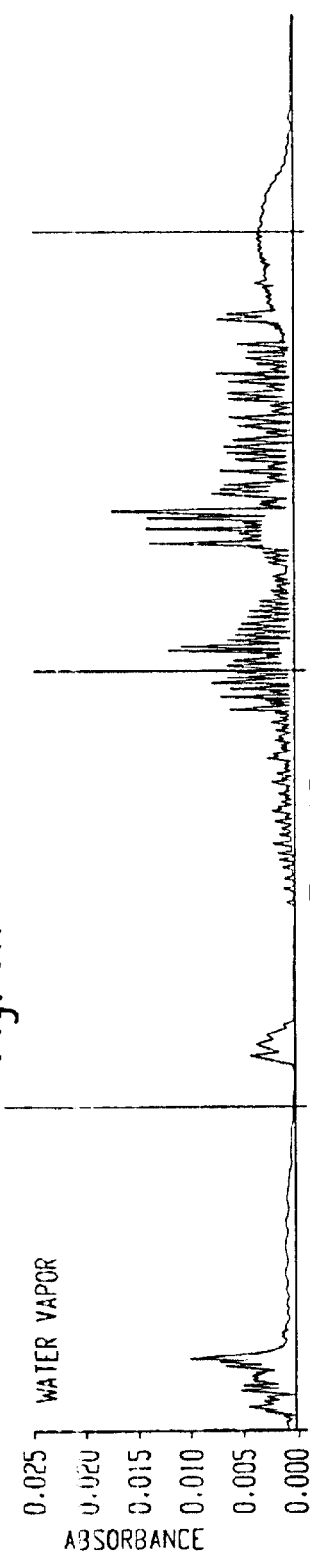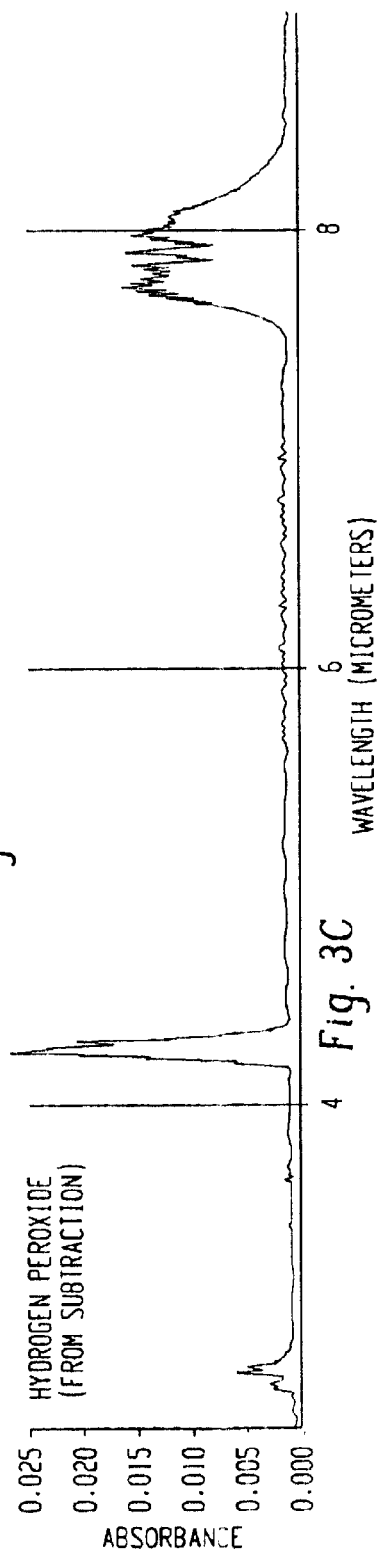
Fig. 3A
Fig. 3B
Fig. 3C

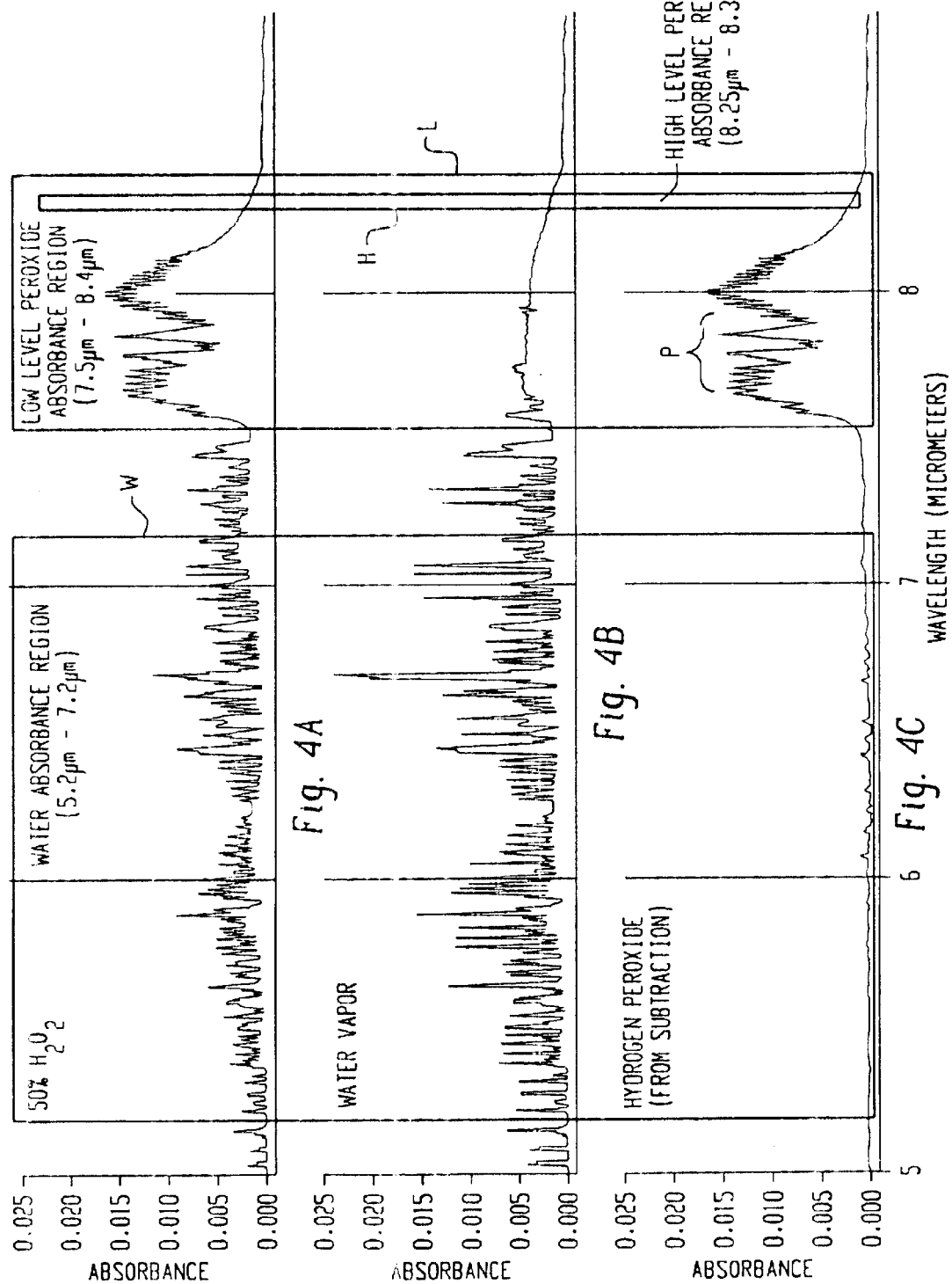

NON-DISPERSIVE MID-INFRARED SENSOR FOR VAPORIZED HYDROGEN PEROXIDE

This application claims the priority of U.S. Provisional Application Ser. No. 60/290,599, filed May 11, 2001.

FIELD OF THE INVENTION

The present invention relates generally to a system and method of vapor-phase decontamination and, more particularly, to a sensor for detecting the concentration of hydrogen peroxide in a two component vapor-phase sterilant. It will be appreciated that the system is also applicable to the detection of the concentrations of other fluid components.

BACKGROUND OF THE INVENTION

Reusable medical instruments and pharmaceutical and biological equipment are generally sterilized before each use. Additionally, reusable containers employed in medical, pharmaceutical, and biological applications, such as glove boxes and incubators, are generally sterilized before each use. In facilities and applications where these types of instruments and containers are used several times a day, it is important to achieve sterilization efficiently and economically. Food packaging materials, such as soda bottles, milk containers, and the like, are also microbially decontaminated prior to filling. At current bottling plant flow rates of a thousand bottles/hour or more, it is desirable to optimize sterilization conditions for rapid sterilization.

Several different methods have been developed for delivering a vapor phase sterilant to an enclosure or chamber for sterilizing the load (e.g., medical instruments or other articles) or interior thereof. In one option, the "deep vacuum" approach, a deep vacuum is used to pull liquid sterilant into a heated vaporizer. Once vaporized, the sterilant vapor is drawn into an evacuated and sealed chamber. In another option, the "flow-through" approach, vaporized sterilant is mixed with a flow of carrier gas that serves to deliver the sterilant vapor into, through and out of the chamber, which may be at slightly negative or positive pressure.

Methods have been developed for optimizing a vapor phase sterilization in a deep vacuum and/or flow-through system. Cummings, et al., U.S. Pat. No. 4,956,145, discloses a deep vacuum method of vapor phase sterilization in which a predetermined concentration of hydrogen peroxide sterilant vapor is maintained in an evacuated, sealed chamber. The amount of liquid sterilant injected into a vaporizer is regulated or adjusted to account for the estimated decomposition of hydrogen peroxide sterilant vapor into water and oxygen in the closed system over time. In a different approach, a predetermined percent saturation is maintained in an open, flow-through sterilization system as disclosed in U.S. Pat. No. 5,445,792.

Childers, U.S. Pat. No. 5,173,258, discloses another flow-through system in which vapor phase hydrogen peroxide is introduced into a recirculating, closed-loop flow of carrier gas. The hydrogen peroxide is introduced and maintained at a predetermined concentration which is selected to optimize the sterilization cycle. The system includes a dryer to dehumidify the recirculating flow, preferably to at least about 10% relative humidity, and thereby prevent moisture buildup resulting from the decomposition of hydrogen peroxide vapor over time. By eliminating moisture build-up, the system can maintain the sterilization chamber at higher concentrations of vapor phase hydrogen peroxide sterilant for longer periods of time (i.e., the predried gas will accept more of the sterilant vapor). Further, to avoid condensation of the sterilant, the relative humidity in the chamber is preferably reduced (e.g., to less than about 30%) prior to introducing the sterilant vapor. After decontamination is complete, the enclosure may be re-dehumidified or conditioned if desired for the selected application.

Gaseous and vapor sterilization/decontamination systems rely on maintaining certain process parameters in order to achieve a target sterility or decontamination assurance level. For hydrogen peroxide vapor sterilization/decontamination systems, those parameters include the concentration of the hydrogen peroxide vapor, the degree of saturation, the temperature and pressure, and the exposure time. By controlling these parameters, desired sterility assurance levels can be successfully obtained while avoiding condensation due to vapor saturation. Existing systems typically monitor the amount of liquid delivered to the vaporization system over time, and, based on temperature, pressure, volume, and (where applicable) flow rate, calculate the theoretical concentration of hydrogen peroxide vapor. The system then correlates some or all of these parameters with empirically derived estimates of hydrogen peroxide decomposition, to arrive at an estimate of the amount of hydrogen peroxide to inject into the system in order to maintain a selected theoretical concentration of hydrogen peroxide vapor. The sterilization performance is then validated empirically via microbiological efficacy testing.

In actual practice, several factors can affect the concentration of components of the vapor, such as decomposition, absorption and adsorption, all due to contact of the gas with various surfaces in the system, and dilution due to evaporation by water vapor from the loads being processed and to decomposition of the sterilant. These effects can vary from load to load and system to system. It is, therefore, desirable to measure the hydrogen peroxide concentration directly. Stewart, et al., U.S. Pat. No. 5,872,359, discloses a hydrogen peroxide sensor system and method of control of a vapor sterilization chamber. The sensor uses near infra-red (NIR) detection at two specific wavelengths, one corresponding to a predominantly hydrogen peroxide peak, the other to a water peak. There is some overlap between the peroxide and water peaks. By manipulating the data, the contribution of water can be subtracted out and the hydrogen peroxide concentration determined.

The present invention provides a new and improved hydrogen peroxide vapor sensor and method of use, which overcomes the above-referenced problems and others.

SUMMARY OF THE INVENTION

In accordance with one aspect of the present invention, a method of microbial decontamination is provided. The method includes exposing an item to be microbially decontaminated to a multi-component vapor which includes hydrogen peroxide and a second vapor component. Hydrogen peroxide in the multi-component vapor is detected by directing multi-chromatic light through the multi-component vapor. The multi-chromatic light includes light of at least a first wavelength range where hydrogen peroxide absorbs but at which second vapor component does not significantly absorb. The first wavelength range includes one or more wavelengths between about 7500 and 8400 nanometers. The absorbance of light which has passed through the vapor is detected in the first wavelength range. The concentration of hydrogen peroxide in the multi-component vapor is determined from the detected absorbance.

In accordance with another aspect of the present invention, a method for determining the concentration of hydrogen peroxide and water in a multi-component vapor is provided. The method includes directing light through the multi-component vapor. The light includes wavelengths in a first wavelength range of the mid infrared spectrum at which hydrogen peroxide absorbs but at which water does not significantly absorb and wavelengths in a second wavelength range of the mid infrared spectrum at which water absorbs but at which hydrogen peroxide does not significantly absorb. Light which has passed through the multi-component vapor is detected in the first wavelength range. Light which has passed through the multi-component vapor in the second wavelength range is detected separately. Concentrations of water and hydrogen peroxide in the multi-component vapor are determined from the light detected in the first and second wavelength ranges.

In accordance with another aspect of the present invention, a decontamination system is provided. The system includes a chamber which receives items to be microbially decontaminated. A source of a gaseous sterilant supplies the gaseous sterilant to the chamber. A sensor system includes a transmitting portion, which directs light through the gaseous sterilant, and a receiving portion which receives light which has passed through the gaseous sterilant. The receiving portion includes a first detector positioned to receive light which has passed through the gaseous sterilant. The first detector detects light in a wavelength range of the mid-infrared spectrum at which a first component of the gaseous sterilant absorbs. A control system controls conditions within the chamber in response to a signal indicative of the light detected by the first detector.

One advantage of at least one embodiment of the invention is that hydrogen peroxide is measured in a Mid-IR wavelength range where water does not significantly absorb, thereby eliminating the need for subtraction of the water vapor contribution to the absorbance measured.

Another advantage of at least one embodiment of the present invention resides in the separate detection of high and low hydrogen peroxide concentrations, thereby reducing the complexity of the detection equipment.

Still further advantages of the present invention will become apparent to those of ordinary skill in the art upon reading and understanding the following detailed description of the preferred embodiments.

BRIEF DESCRIPTION OF THE DRAWINGS

FIG. 3A is a plot of absorbance for a vapor mixture of 50% hydrogen peroxide, 50% water over the wavelength range 2.5–9 microns;

FIG. 3B is a plot of absorbance for pure water vapor over the wavelength range 2.5–9 microns;

FIG. 3C is a plot of absorbance for hydrogen peroxide vapor over the wavelength range 2.5–9 microns obtained by subtracting the absorbance of FIG. 3B from those of FIG. 3A;

FIG. 4A is an enlarged plot of absorbance for a vapor mixture of 50% hydrogen peroxide, 50% water over the wavelength range 5–9 microns;

FIG. 4B is an enlarged plot of absorbance for pure water vapor over the wavelength range 5–9 microns;

FIG. 4C is an enlarged plot of absorbance for hydrogen peroxide vapor over the wavelength range 5–9 microns obtained by subtracting the absorbance of FIG. 3B from those of FIG. 3A;

DETAILED DESCRIPTION OF THE PREFERRED EMBODIMENT

Figure 1:
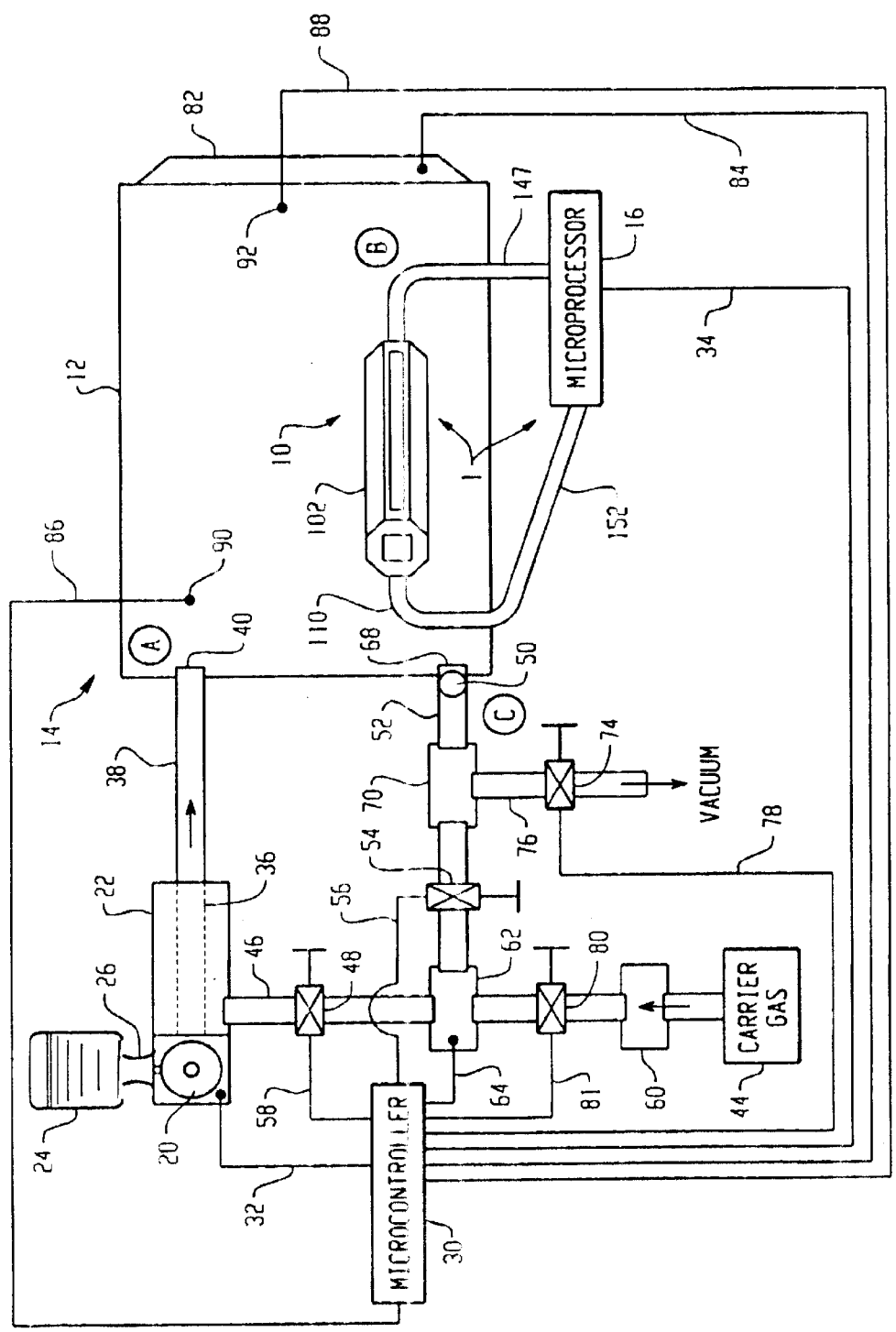
FIG. 1 is a schematic illustration of a real-time monitoring and control system for optimizing parameters including the concentration of one or more sterilant vapors in a multi-component vapor sterilization process.

With reference to FIG. 1, a sensor system 1, suited to the detection of a fluid component in a multi-component fluid, is shown. In a preferred embodiment, the multi-component fluid includes a gaseous oxidant. For example, the multi-component fluid is a sterilant vapor, which comprises hydrogen peroxide vapor generated from an aqueous hydrogen peroxide solution. Preferably, the hydrogen peroxide solution has a concentration of hydrogen peroxide of from 5–95% by weight, more preferably, from about 30–40% by weight, the balance being water.

Although the words "sterilant" and "microbial decontaminant" and similar terms are used interchangeably, it will be understood that the system and method disclosed are applicable to all levels of microbiological decontamination, including sterilization, disinfection, sanitization, and the like. Items to be microbially decontaminated include medical, dental, mortuary, or pharmaceutical instruments, which may be contaminated with microorganisms deposited on the instruments during a surgical procedure, and devices intended as surgical implants that require terminal sterilization upon completion of the manufacturing process, although other items to be microbially decontaminated are also contemplated. Microbial decontamination is also intended to include the destruction or inactivation of other harmful biological species, such as prions.

The term "decontaminate" is also intended to encompass chemical decontamination of articles, such as the destruction of hazardous chemicals, particularly nerve and blister agents, such as nerve gases and their residues, by gaseous oxidants. Nerve gases include ethyl-N, N dimethyl phosphoramino cyanidate (commonly known as Tabun or agent GA), isopropyl methyl phosphonofluoridate (Sarin or agent GB), o-ethyl-S-(2-diisopropyl aminoethyl) methyl phosphono-thiolate (agent VX). Articles, such as clothing or vehicles, or entire rooms or other enclosures, which have been contaminated with such chemical agents may be decontaminated by the processes described herein. It will be appreciated that both chemical and microbial decontamination may be carried out in a single process, where the gaseous oxidant, e.g., hydrogen peroxide vapor, has both chemical and microbial decontamination properties.

The sensor system 1 includes a sensor or probe 10, preferably a mid infrared (MIR) sensor, which is used to detect the concentration of one or more of the components of a fluid, such as a gaseous component of a multi-component sterilant vapor or a component in a liquid. By mid infrared, it is meant that the sensor detects a wavelength or range of wavelengths in the range of from about 2–10 micrometers (microns), i.e., 2000–10,000 nanometers. Most preferably, for hydrogen peroxide detection, the sensor 10 detects wavelengths in the region of a hydrogen peroxide peak, the region being one in which water does not show significant absorption. It will be appreciated, however, that the choice of wavelength is dependent on the component or components to be detected and the presence or absence of interfering peaks from other components of the multi-component fluid. Sensors which detect in the near infra red (NIR) or in other regions of the electromagnetic spectrum are also contemplated. The term "light" is used herein to encompass both visible and non-visible portions of the electromagnetic spectrum including IR wavelengths.

The sensor is suited to use in static and in flow-through systems at ambient, sub-atmospheric, or above-atmospheric pressures. In an ambient system, the multi-component fluid may be transported in a carrier gas, such as air. Other inert gas carriers, such as oxygen, nitrogen, or helium, may also be used. In a deep vacuum sterilization chamber, the internal pressure is preferably in the range of about 0.1 to 10 torr.

When hydrogen peroxide vapor is the sterilant vapor used, the concentration of hydrogen peroxide vapor is most preferably close to or at the saturation level of the vapor, as long as condensation or saturation is avoided.

It is contemplated that other gaseous sterilants may be employed in the system, alone or in combination with water or carrier gases, and be subjected to the method described herein. Exemplary gaseous sterilants include oxides of halogens, such as chlorine dioxide, alkene oxides, such as ethylene oxide, alcohols, such as ethanol, peracids, such as peracetic acid, ozone, lactams, such as β-propyl lactam, and mixtures of sterilants, such as hydrogen peroxide/peracetic acid/water mixtures, alcohol/hydrogen peroxide/water mixtures, ethylene oxide/water mixtures, and the like. For purposes of describing the preferred embodiments of the flow-through system, the carrier gas and the sterilant vapor discussed will be respectively air and vapor phase hydrogen peroxide generated from aqueous hydrogen peroxide solution. Thus, water vapor will be present in variable concentrations in the sterilization chamber.

The sensor probe 10, is mounted within a vessel 12, such as a sterilization chamber, or in some portion of a sterilization system 14 which is in fluid communication with the sterilization chamber 12. The probe measures the absorbance by one or more components, e.g., sterilant vapors, in the chamber or system. The absorbance measurements are used to calculate a concentration (or parameter related to concentration) of the component in the vapor. The measurements are used for feedback control of conditions within the chamber. For example, by controlling at least one of the temperature of the vapor, the rate of introduction of the component to the chamber, the concentration of one component in the multi-component vapor, the concentration of a second component in the multi-component vapor, or the pressure of the multi-component vapor within the chamber, selected conditions within the chamber are maintained, or the exposure time (the length of time an item to be sterilized spends in contact with the vapor) varied, to achieve optimal conditions for sterilization.

In the sensor system 1, the absorbance detected by the probe is transmitted from the probe 10 to a microprocessor 16 programmed to calculate the concentration of hydrogen peroxide vapor in the sterilization chamber. The output of the microprocessor is preferably in the form of a digital signal. Preferably, the microprocessor has been pre-programmed with calibration values derived from controlled experiments to calibrate the instrument with known concentrations of hydrogen peroxide vapor in the multi-component vapor. A single microprocessor 16, such as a personal computer (PC), preferably receives signals from several such probes 10, positioned at suitable locations A, B, C around the chamber 12 or elsewhere in the system 14.

In response to the signal received from the probes 10, the microprocessor 16 controls operation of the system 14 to achieve preselected sterilization conditions in the chamber 12. In particular, the microprocessor controls opening and closing of a liquid hydrogen peroxide injection valve 20 which regulates the flow of liquid hydrogen peroxide into a vaporizer 22, so as to maintain an optimum concentration of hydrogen peroxide vapor in the sterilization chamber.

A liquid sterilant reservoir 24 contains a bulk supply of the liquid sterilant, a liquid mixture of hydrogen peroxide and water in the preferred embodiment. The liquid in the reservoir 24 is preferably an aqueous solution of hydrogen peroxide between 3 and 98% by weight, more preferably, 10–50% hydrogen peroxide by weight, and, most preferably, 30–35% hydrogen peroxide by weight. Aliquots (or a continuous feed) of liquid are metered from the reservoir 24 through the valve 20 and into the vaporizer 22 via a sterilant supply line 26.

With continued reference to FIG. 1, items to be sterilized or chemically decontaminated are loaded into the sterilization chamber 12 or passed therethrough on a conveyor system (not shown). Alternatively, chamber 12 is a container, such as a glove box, which needs to be sterilized. The items may include medical, dental, mortuary, or pharmaceutical instruments, devices intended as surgical implants, and the like. The sterilization chamber 12 is supplied with a vapor formed from the liquid sterilant contained in the liquid sterilant reservoir 24.

A microprocessor-controller 30 controls the selective opening and closing of the valve 20. An electrical connector 32 connects the microprocessor-controller 30 with the valve 20. Microprocessor 16 and controller 30 are shown in FIG. 1 as separate components, linked by a connector 34. It will be appreciated, however, that the two microprocessors 16 and 30 may be replaced by a single microprocessor controller. The microprocessor 16 and 30 together comprise a control system for the system 14.

The vaporizer 22 is equipped with a heated surface 36. The entire aliquot of sterilant liquid (sterilant and water) is flash vaporized in the vaporizer 22 to form the sterilant vapor, such that the relative composition of the vaporized sterilant is substantially the same as that of the liquid sterilant from which it was vaporized. The vaporized sterilant passes from the vaporizer along a vapor inlet line 38 and through an inlet port 40 into the sterilization chamber 12.

FIG. 1 shows a flow-through sterilization system 14, although it will be appreciated that the sensor may also be used in static systems. In a flow through system, a carrier gas continuously flows from a carrier gas source 44 through an inlet line or tube 46 into the vaporizer 22. The carrier gas and the vaporized sterilant combine in the vaporizer and the combined carrier gas and sterilant vapor pass through the inlet port 40, into the sterilization chamber 12. The carrier gas source 44 may be a compressor (e.g., for air), or a cylinder or tank of compressed gas. Or, for systems operating at negative gauge pressure, air at atmospheric pressure may be permitted to enter the system at a selected rate. Flow of the carrier gas into the system is regulated by a carrier gas inlet valve 48. A pump 50 is optionally used to pump the vapor into or out of the chamber.

The system 14 shown in FIG. 1 is a recirculating system, although one-pass systems are also contemplated. The flow of recirculating carrier gas and sterilant vapor through a return flowpath along a fluid line 52 is controlled by a recirculating flow control valve 54. In the case of a recirculating system, the valves 54 and 48 are preferably operated under the control of a process control portion of the microprocessor-controller 30 or controller 16, communicated via electrical connectors 56 and 58.

Referring still to FIG. 1, the incoming carrier gas preferably passes through a sterile filter 60 in the inlet line 46 and may optionally be dried while passing through a carrier gas dryer 62. In a recirculating system, the dryer may also be operated to control the water content of the recirculating carrier gas. The dryer 62 may be operated under the control of the microprocessor-controller 30 or controller 16, communicated via an electrical connector 64.

In the embodiment of FIG. 1, the carrier gas and spent vapor exit the sterilization chamber 12 by means of an outlet port 68, and passes along the return flowpath via line 52, through a catalytic decomposition device 70, and through the heater/dryer 62 for heating or drying. The return flowpath joins the carrier gas inlet line 46 at the heater/dryer 62. The carrier gas is then recirculated through the closed-loop flow-through system.

The flow-through system may also be operated as an open system, by closing the valve 54 and opening a valve 74, in an outlet line 76, thereby removing carrier gas from the chamber 12 to atmosphere. Preferably, operation of the valve 74 is controlled by the microprocessor-controller via an electrical connector 78, as shown in FIG. 1. The catalytic decomposition device 70 is operated to decompose any remaining sterilant vapor into harmless by-products, leaving the recirculating carrier gas free of sterilant and requiring a new supply of sterilant vapor to reach its selected concentration. Alternatively, the carrier gas may be recirculated with its load of remaining sterilant vapor, and in this case, a quantity of sterilant vapor will be added sufficient only to replenish the sterilant vapor to its selected concentration.

If the apparatus shown in FIG. 1 is to be operated as a deep-vacuum sterilization system, the carrier gas apparatus just described will either not be used and closed off from the inlet line 46 a valve 80, connected to the microprocessor controller 30 by a valve 81, or not be part of the apparatus at all. In this embodiment, the valves 54 and 80 remain closed at all times, except to open the system to an external atmosphere and release the deep vacuum.

The outlet port 68, in a deep-vacuum embodiment of FIG. 1, like the flow-through embodiment, is attached first to the catalytic decomposition device 70, thence to a vacuum pump (not shown) via the outlet line 76. The vacuum pump creates the deep vacuum selected for such an embodiment. As in other embodiments, the catalytic decomposition device 70 decomposes hydrogen peroxide into water and oxygen.

If the sensor probe 10 is employed with such a closed flow-through system, use of the catalytic decomposition device 70 is optional. As the sensor system 1 can detect the concentration of hydrogen peroxide or other sterilant gases on a real-time basis, only sufficient vapor need be added to the chamber to maintain the selected concentration of hydrogen peroxide or other sterilant vapor in the sterilization chamber 12.

The sterilization chamber 12 is preferably equipped with a heater 82, for providing heat as needed for sterilizations carried out at temperatures above room temperature. The heater 82 is operated under the control of the microprocessor-controller 30, via an electrical connector 84. Alternatively or additionally, the carrier gas may be heated prior to its introduction into either the system as a whole or the sterilization chamber 12.

The microprocessor-controller 30, as shown in FIG. 1, is preferably connected via electrical connectors 86, 88 with a plurality of sensors 90, 92, disposed with the sterilization chamber 12, in addition to the sensor probe 10. These sensors provide information on, e.g., temperature, pressure, humidity, and other relevant conditions within the chamber 12. This information is used by the microprocessor portion of the microprocessor-controller 30 according to its programming to provide control of operation of the sterilizer system via the controller portion of the microprocessor-controller 30.

The system of claim 1 may be used for chemical decontamination of items although it is to be appreciated that all gases leaving the chamber are preferably passed though a further treatment process to ensure that all hazardous chemical agents are removed prior to release of the gases into the atmosphere. Preferably, a single pass process is used to ensure that hazardous materials are not recirculated. Additionally, sensors (not shown) in the outlet line 76 detect for minute traces of the hazardous materials which may remain and the controller is instructed to continue the decontamination process at least until the level of hazardous materials in the outlet vapor is reduced to a safe level.

Figure 2:
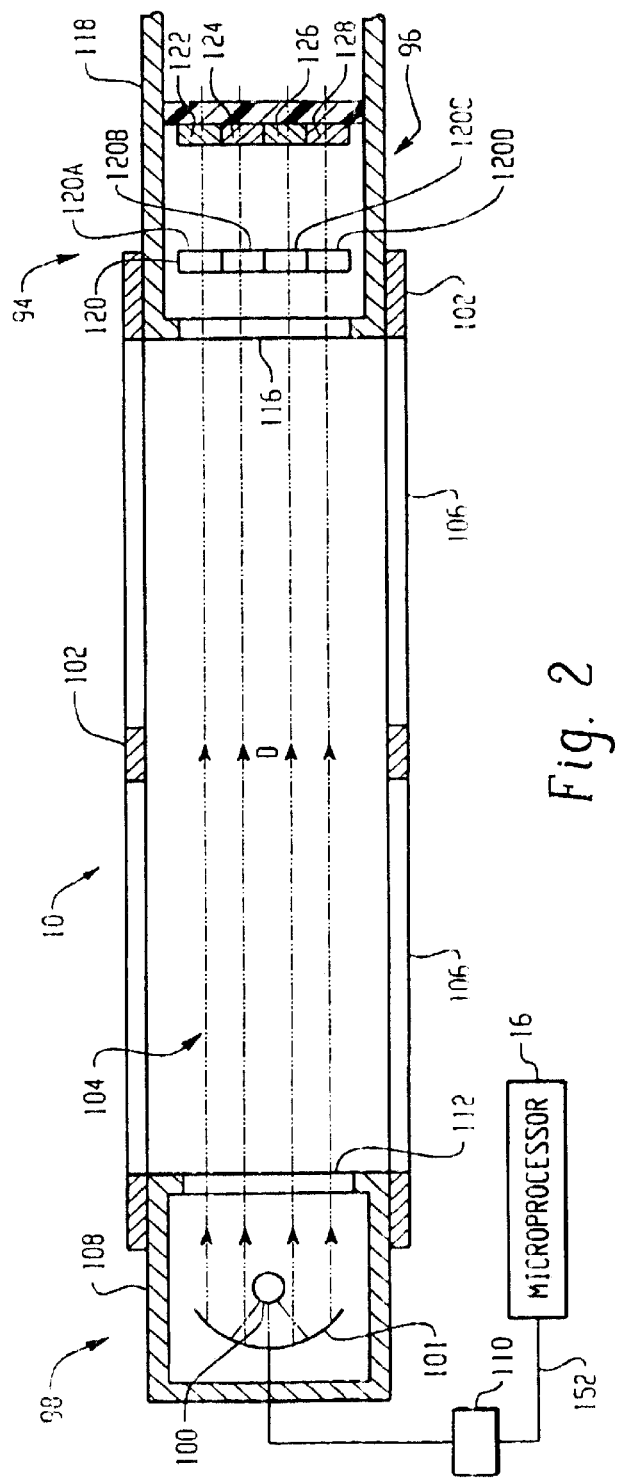
FIG. 2 is a schematic illustration of a first embodiment of the infrared sensor system of FIG. 1.
Figure 13:
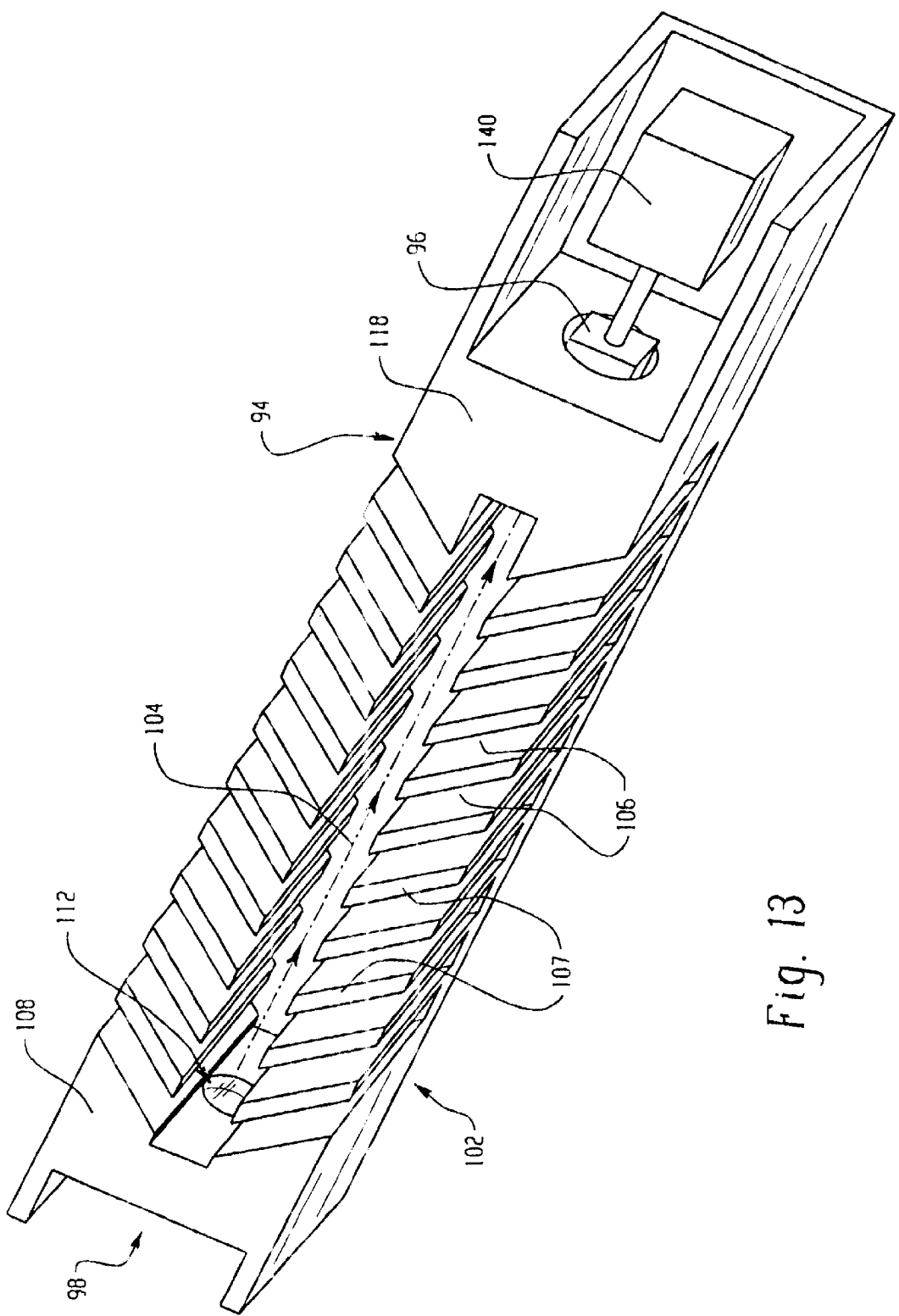

With reference also to FIG. 2, a first embodiment of a sensor probe 10 is shown. The sensor probe 10 includes a receiving portion 94, including a detection system 96. The probe also includes a transmitting portion 98, which includes a radiation source 100, such as an IR source. A collimator 101, such as a parabolic mirror, provides a collimated beam D of IR radiation. The detection system 96 and radiation source 100 of FIGS. 1 and 2 are located within the chamber 12. Alternatively, the source and detector are located outside the chamber 12 and are connected therewith by fiber optic cables, or the like, as discussed in greater detail below. The detection system 96 and radiation source 100 are separated from each other by a space through which the vapor passes. In the embodiment of FIG. 1, a hollow body 102 acts both as a positioner for maintaining the alignment of the transmitting portion 98 and receiving portion 94, and as a shield to prevent objects within the sterilization chamber 12 from obstructing an energy path 104 between the transmitting and receiving portions of the sensor. The body 102 comprises a plurality of openings 106, such as slots, holes, or other perforations, through which the sterilant vapor to be measured may freely pass. The openings 106 allow free passage and exchange of the sterilant vapor into and out of the path 104 of the radiation beam, whereby the sterilant vapor interacting with the radiation is representative of that in the sterilization chamber 12. Preferably, the openings 106 in the body 102 have the maximum size possible so as to allow the sterilant vapor to pass most freely, consistent with preventing objects in the sterilization chamber 12 from obstructing the energy path 104. The body also provides rigidity to the system to minimize vibration and maintain optical alignment. The openings are preferably configured so as to prevent stray light from impinging on the detection system 96. For example, the openings 106 are configured as spaces between louvers 107, as shown in FIG. 13.

Preferably, two or more sensor probes 10 are used, for example, in positions A, B, and/or C (FIG. 1). Position A has the sensor probe 10 mounted adjacent the inlet port 40. Since position A is closest to the inlet port 40, it may result in the highest readings for hydrogen peroxide concentration. Position B has the sensor probe in a position intermediate the inlet port 40 and the outlet port 68. Position B may be closest to the load to be sterilized, and the hydrogen peroxide concentration there may be more representative of the concentration experienced by the load. Position C has the sensor probe in the return line 52. This position may yield the lowest readings for hydrogen peroxide concentration, but if it is desired to maintain some threshold minimum hydrogen peroxide concentration, this position should give the most accurate results. The actual placement of the sensor probe(s) 10 may best be determined by the user, in view of the exact application for which the sterilization system is employed. More than one sensor probe 10 can be mounted within the system, and the microprocessor may be programmed to select only one or more than one sensor probe 10 when a plurality of the sensor probes are employed.

All portions of the sensor probe 10 and of the entire system that will come into contact with hydrogen peroxide are preferably made of a material which is both inert to hydrogen peroxide and which does not absorb or adsorb hydrogen peroxide. Accordingly, the body 102 is preferably made of passivated or electro-polished stainless steel or passivated aluminum. Other materials which do not interact deleteriously with hydrogen peroxide include glass, polytetrafluoroethylene (PTFE, Teflon™), and viton. The body 102 preferably has openings at either end for secure attachment of the transmitting portion and receiving portion. The body preferably is prismatic in shape and has an angular cross section, such as a octagonal, hexagonal, or square cross section. The detection system 96 and transmitting portion 98 are suitably shaped to be received within the opposed open ends of the body. The angular body reduces the chance that the body 102 will roll if removed from the sterilizer and placed on a flat surface, which could cause damage to sensitive components of the probe 10. Preferably the body 102 includes means for maintaining the transmitting member and receiving member in proper alignment, so as to maximize signal strength therebetween. Sensor probe 10 may also include mirrors and/or lenses for focusing and realigning the beams of radiation carried by the transmitting member and receiving member.

The microprocessor 16 is preferably programmed to calculate the concentration of hydrogen peroxide in the sterilization chamber 12 based on the information transmitted by the receiving portion 94. The microprocessor 16 is operably connected to the microprocessor-controller 30. It will be understood that the microprocessor 16 may be combined with the microprocessor portion of microprocessor-controller 30 into a single microprocessor, and that the output of this single microprocessor would in turn provide signals to a controller. If the microprocessors are combined, the output preferably provides a digital signal, e.g., a serial data stream, directly to a controller or via a digital interface or connection to control operation of the sterilization chamber 12 in a manner similar to that described for the output of the microprocessor-controller 30.

The controller 30 and/or microprocessor 16 preferably controls some or all of the following parameters: heat applied by the chamber heater, carrier gas flow rates, the exposure time of items, composition of the sterilant liquid to be injected into the vaporizer, and other aspects of the system 14 to ensure optimal sterilization conditions are being maintained and to ensure that the items being sterilized are exposed for a sufficient time to achieve sterilization. These changes can be made on a real time basis, using the calculated or received values of sterilant concentration, water concentration, pressure, temperature, and the like and making adjustments, as necessary to maintain selected values or to optimize conditions for sterilization. For example, the controller 16 may register a sudden drop in temperature in the chamber and, in response, temporarily reduce vapor input to avoid condensation and lengthen the exposure time to compensate for this.

Alternatively, the microprocessor 16 is programmed to receive data from the sensor probe 10, and to calculate therefrom the concentration of sterilant vapor in sterilization chamber 12. In this embodiment, the microprocessor-controller 30 is programmed to receive the sterilant vapor concentration values determined by the microprocessor 16, and the temperature, pressure, humidity, and other parameters of the sterilizing chamber 12 made available to it. The microprocessor 16 may also be programmed to calculate the qualities of sterilant vapor needed to be added to the sterilizing fluid or sterilization chamber 12 and to signal the microprocessor-controller 30 via the connector 34 to cause the sterilant liquid to be injected into the vaporizer 22, accordingly, to produce the sterilant vapor.

The IR source 100 and IR detection system 96 are respectively capable of producing and quantitatively detecting IR radiation at least at one selected wavelength. The IR source is preferably a multi-chromatic source capable of providing radiation at substantially the selected wavelength (s) or across a range or spectrum of wavelengths. The IR detection system is preferably able to detect the strength of both the returning signal and of the transmittal signal, and to provide this information to the microprocessor 16.

Output from the source of IR radiation 100 is directed, optionally first through a transmitter fiber optic cable, through the vapors contained in the sterilization chamber 12. Radiation not absorbed by the multi-component vapor is transmitted, optionally through a receiver fiber optic cable, to the IR detection system 96.

With reference to FIGS. 3A, 3B and 3C, it has been found that, within the Mid-IR range, hydrogen peroxide and water produce distinctly separate peaks. By way of example, plots were run over the wavelength range of 2.5–9.5 micrometers. FIG. 3A is a plot for a vapor mixture of 50% hydrogen peroxide, 50% water. FIG. 3B is a plot for pure water vapor (although unfortunately, in this example, a small amount of hydrogen peroxide remained in the system following the mixed scan). FIG. 3C demonstrates how the hydrogen peroxide can be separated out from the water by subtraction of the plot of FIG. 3B from that of FIG. 3A. A mixed hydrogen peroxide and water peak can be seen around 2.5 to 3 microns. A peak for carbon dioxide is observed at around 4–4.5 microns, since this was not excluded from the system. Water peaks are observed between about 5 and 7.5 microns. Beyond around 7.5 microns (specifically, between about 7.5 microns and 8.4 microns) are the coupled hydrogen peroxide peaks. As can be seen from FIG. 3B, there is little or no absorption due to water in this region such that the response is due almost entirely to hydrogen peroxide. Thus, complex subtraction techniques are not necessary for determining the hydrogen peroxide present if this region of the spectrum is employed. The entire response can be assumed to be due to hydrogen peroxide.

Thus, by selecting a detection wavelength or range of wavelengths in the region of the 7.5–8.4 micron hydrogen peroxide peak, hydrogen peroxide can be detected without the need for detecting at both a predominantly hydrogen peroxide peak and at a predominantly water peak and then subtracting out the contribution of water to the hydrogen peroxide peak. It will be appreciated, however, that if a wavelength is selected where there is some overlap between the component peaks, a subtraction method can be used to eliminate the contribution of water, or other selected component, from that of the selected sterilant component.

FIGS. 4A, B, and C show the region of the spectrum between 5 and 9 microns corresponding to plots 3A, B, and C. In a preferred embodiment, the sensor detects water by using the region W between about 5.2 and 7.2 microns (either by integrating the entire spectrum in this range or by selection of one or more narrower ranges in the region of the peaks). The sensor preferably detects hydrogen peroxide in the region between about 7.5 and 8.4 microns (either by integrating the entire spectrum in this range or by selection of one or more narrower ranges, e.g., at about 7.75 or 8.1 microns).

With reference once more to FIG. 2, the transmitting portion 98 includes a housing or casing 108 in which the IR radiation source 100 is mounted. Preferably, a modulated light source power supply 110 causes a modulated radiation source 100 to emit a beam D of modulated (pulsed on and off) light in a range of wavelengths, preferably, encompassing the range of from about 5 to 9 microns (5,000–9,000 nm), which passes through an IR-permeable window 112 in the housing and through the vapor to be detected on the hollow body 102. IR radiation which is not absorbed by the vapor passes through a window 116 in a housing or casing 118 of the sensor probe detection system 112. While non-modulated light sources are also contemplated, a modulated source provides the controller with a means of rejecting background noise.

The casings 108, 118 may be mounted within the chamber 12 or other part of the system. Or, it may be positioned outside the chamber, with the window 116 positioned in an opening in the chamber wall so as to receive the beam D. Or, the window may be connected with a light pipe, such as a fiber optic cable, which carries the beam D from the chamber to the window.

The IR radiation then passes through an optical filter system 120 which filters out wavelengths outside the region of interest. In one embodiment, the filter system 120 comprises several filter portions 120A, 120B, 120C, and 120D (four are shown in FIG. 2, although it is also contemplated that fewer or more than four filter portions may be used). Each filter portion is selective for (i.e., transmissive to) a particular wavelength or wavelength range of the mid-IR spectrum. The filtered IR light from each of the four filter portions strikes a corresponding detector 122, 124, 126, 128, arranged to receive light only from the corresponding filter portion. Each detector is sensitive to a wavelength or wavelength range which encompasses at least a portion of the wavelength range transmitted by the corresponding filter portion. It will be appreciated that the detectors may be sensitive to substantially broader wavelength ranges than those transmitted by their corresponding filters, since only the transmitted wavelengths will be detected. Alternatively, the detectors are sensitive to a much narrower wavelength band than the filter portions, the detectors doing the primary wavelength selecting in this case. If the detectors are sufficiently sensitive, filter portions 120 A, B, C, and D may be replaced by a single filter 120 which filters all the light received by the detectors, or the filter system 120 may be eliminated entirely. In all cases, the filter portion, its corresponding detector, or a combination of filter portion and detector, is selective for a particular wavelength or wavelength range.

The first detector 122 is sensitive to radiation in a wavelength range $\lambda_1$, transmitted by the first filter portion 120A. Range $\lambda_1$ preferably corresponds to all or a portion of the broad hydrogen peroxide range L in FIG. 4 (e.g., from about 7.5–8.4 microns, or a portion of this range). A second detector 124 is sensitive to radiation in a wavelength range $\lambda_2$, which is preferably spaced from $\lambda_1$, and corresponds to the water range (e.g., from about 5.2–7.2 microns). A third detector 126 is sensitive to radiation in a wavelength range $\lambda_3$, which is spaced from $\lambda_1$ and $\lambda_2$, and corresponds to a range where neither hydrogen peroxide nor water vapor absorbs (e.g., from about 4.2–4.6 microns). This detector may be used as a reference to determine the intensity of the transmitted light which is then used to normalize the signal from the other detectors for fluctuations in the intensity of the light source. Absorbance values are then calculated as the log of the ratio of normalized intensity before sterilant vapor was introduced to the normalized intensity in the presence of the sterilant vapor, i.e.:

$$\text{Absorbance} = \frac{(I_1/I_2)}{(I_3/I_4)}$$

where $I_1$=Light intensity before the introduction of sterilant vapor at $\lambda_1$;

$I_2$=Light intensity before the introduction of sterilant vapor at $\lambda_3$;

$I_3$=Light intensity in the presence of sterilant vapor at $\lambda_1$; and $I_4$=Light intensity in the presence of sterilant vapor at $\lambda_3$.

The fourth detector 128 optionally acts as a second reference. Preferably, one of the reference detectors 126 detects in a wavelength range below the water and hydrogen peroxide peaks while the other 128 detects in a range above the peak. Alternatively, the second reference is omitted.

In another embodiment, the first detector 122 detects wavelengths covering all or substantially all of wavelength range L of the hydrogen peroxide peak (e.g., from about 7.5–8.4 microns), while the fourth detector 128 detects a narrower portion of the hydrogen peroxide peak corresponding to wavelength range H (e.g., from about 8.25–8.3 microns), which is preferably away from the peak. In this embodiment, the controller uses signals from one or other of the detectors 122, 128, depending on whether the hydrogen peroxide concentration is high or low.

For example, the sensor system 1 integrates the entire range between about 7.5 and about 8.4 microns, as shown by block L (or a range encompassing one or more of the peaks) for detecting hydrogen peroxide concentrations which are relatively low (e.g., from about 0.001 mg/L to 0.1 mg/L, i.e., about 1–100 ppm). When the hydrogen peroxide concentration is high (e.g., from about 0.1–30 mg/L), the sensor uses the narrower (or lower absorbance) range, shown by block H, which is preferably away from the peak region P. In the H region, the hydrogen peroxide signal, i.e., total absorbance, is much weaker (perhaps about 10% or less of the signal strength in the L block). Preferably, as shown in FIG. 4, the range selected for high concentrations is towards the upper end of the range, e.g., between about 8.25 and 8.35 microns, where water shows little or no absorption. In quantitative terms, a given hydrogen peroxide concentration will preferably provide an absorbance signal in the wavelength range of the low concentration block L which is at least two times, more preferably, at least ten times that of the corresponding absorbance in the high concentration block H, and most preferably, at least 20 times that of the absorbance signal in the block H, although the most preferred ratio will depend on the range of concentrations to be detected. As can be seen from FIG. 4, the ranges selected for the high H and low L hydrogen peroxide levels may be overlapping, or may be spaced from each other. For example, as shown in FIG. 4, the absorbance of hydrogen peroxide at $\lambda_1$ may be from about 2 to about 20 times or more that of the absorbance at $\lambda_4$. The fourth detector 128, in this embodiment, is sensitive to a narrow range $\lambda_4$ (e.g., from about 8.25–8.3 microns), which may be spaced from, or overlapping $\lambda_1$, corresponding to the block H in FIG. 4.

In all the above embodiments, the detectors 122, 124, 126, and 128 are preferably sufficiently spaced from the window 116 that they are unaffected or substantially unaffected by stray IR, for example, resulting from a warm body, such as a person, moving close to the detection system 96. That is, the casing 118 functions as a collimator to block off axis radiation from reaching the detector. The longer the collimator, the narrower the field of view. Optionally, additional collimator vanes, e.g., a + shaped collimator between the detector elements, are also contemplated. The closer the vanes, the narrower the field of view. Further, while the filter system 120 is shown as being spaced from the detectors, the filter system is preferably closely adjacent or in contact with the detectors such that there is little or no light from one filter portion which is received by a detector other than its corresponding detector.

Figure 5:
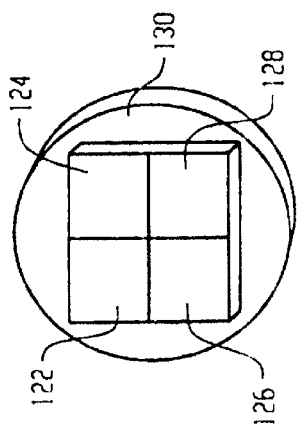
FIG. 5 is a top perspective view of the detection system of FIG. 2.

As shown in FIG. 5, the detectors 122, 124, 126, 128 are laid down on a common support or substrate 130, such as a silicon chip or ceramic grid. For example, the detectors are arranged in a square shape, each detector occupying one corner of the square.

Figure 6:
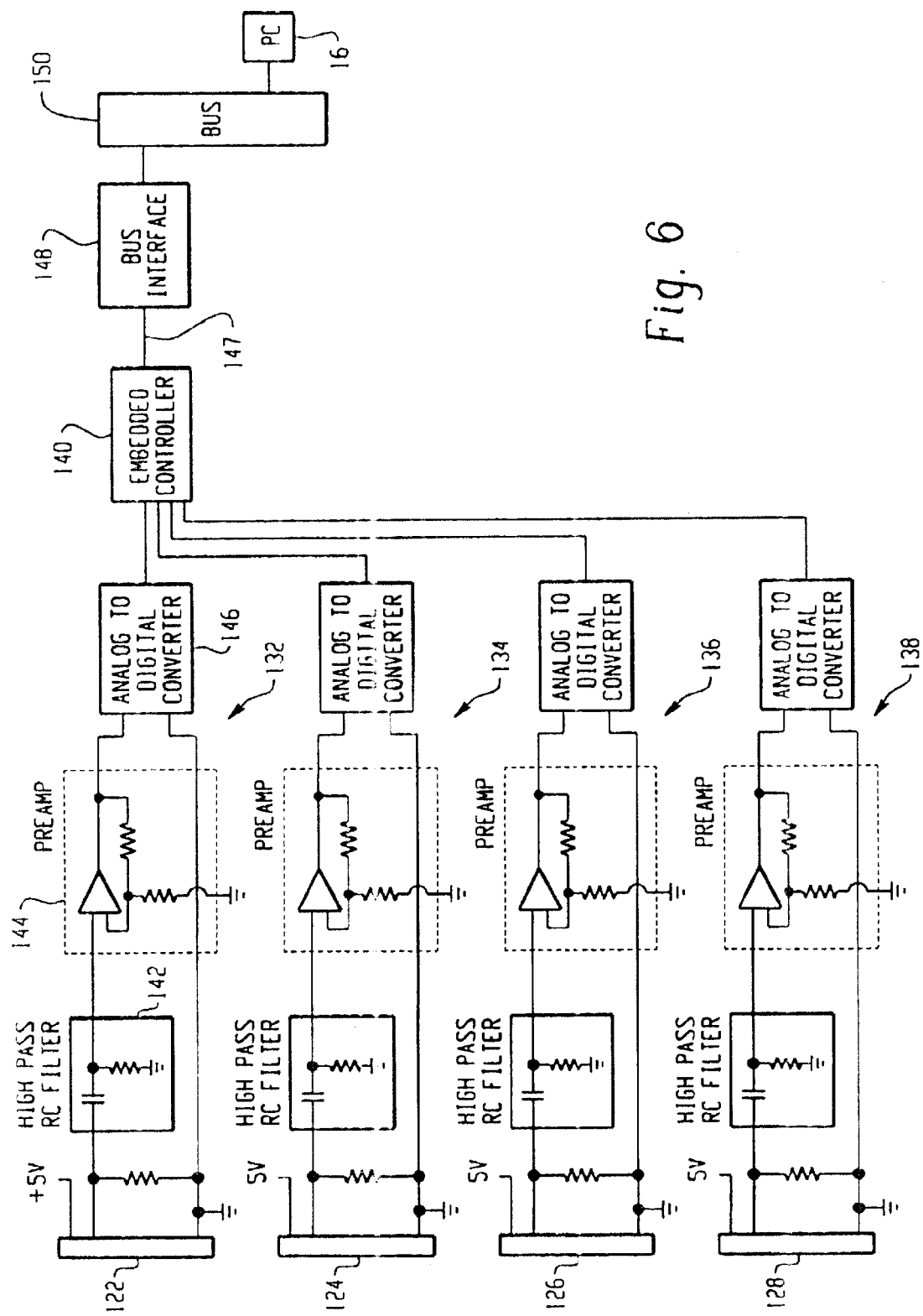
FIG. 6 is a schematic view showing electronic components of the detection system of FIG. 2.

With reference also to FIG. 6, electrical signals from each of the detectors 122, 124, 126, 128 are transmitted via electrical pathways to an embedded controller 140, mounted to or within the substrate 130. The circuitry 132, 134, 136, 138 for transmitting the signal to the embedded controller 140 is the same for each detector, and for convenience will be described with reference to the detector 122. Preferably, a high pass RC filter 142 removes any DC component of the signal. A preamplifier 144 amplifies the signal. The embedded controller 140 may be configured to accept analog signals. More preferably, an analog to digital converter 146 is used to convert the filtered and amplified signal to a digital signal.

The embedded controller sends the signals from each of the four detectors 122, 124, 126, 128 to the controller 16, via an electrical connector 147, which is connected with a bus interface 148 and bus 150. The controller receives the four signals and analyzes them in sequence, although not necessarily in the order illustrated in FIG. 6. The controller 16 also receives signals from the light source via an electrical connector 152. The controller uses the modulation frequency of the light source in calculations to eliminate background noise. The embedded controller 140 may be used to both receive the signals from the detectors 122, 124, 126, 128 and also to control the modulation of the light source 100. Either the embedded controller or the controller 16 performs the analysis to convert the detector signals into concentration information.

An advantage of this embodiment is that it needs no moving parts, which reduces the likelihood of maintenance costs. However, where size or costs of the detectors are a factor, other embodiments employing fewer detectors may be preferred.

Figure 7:
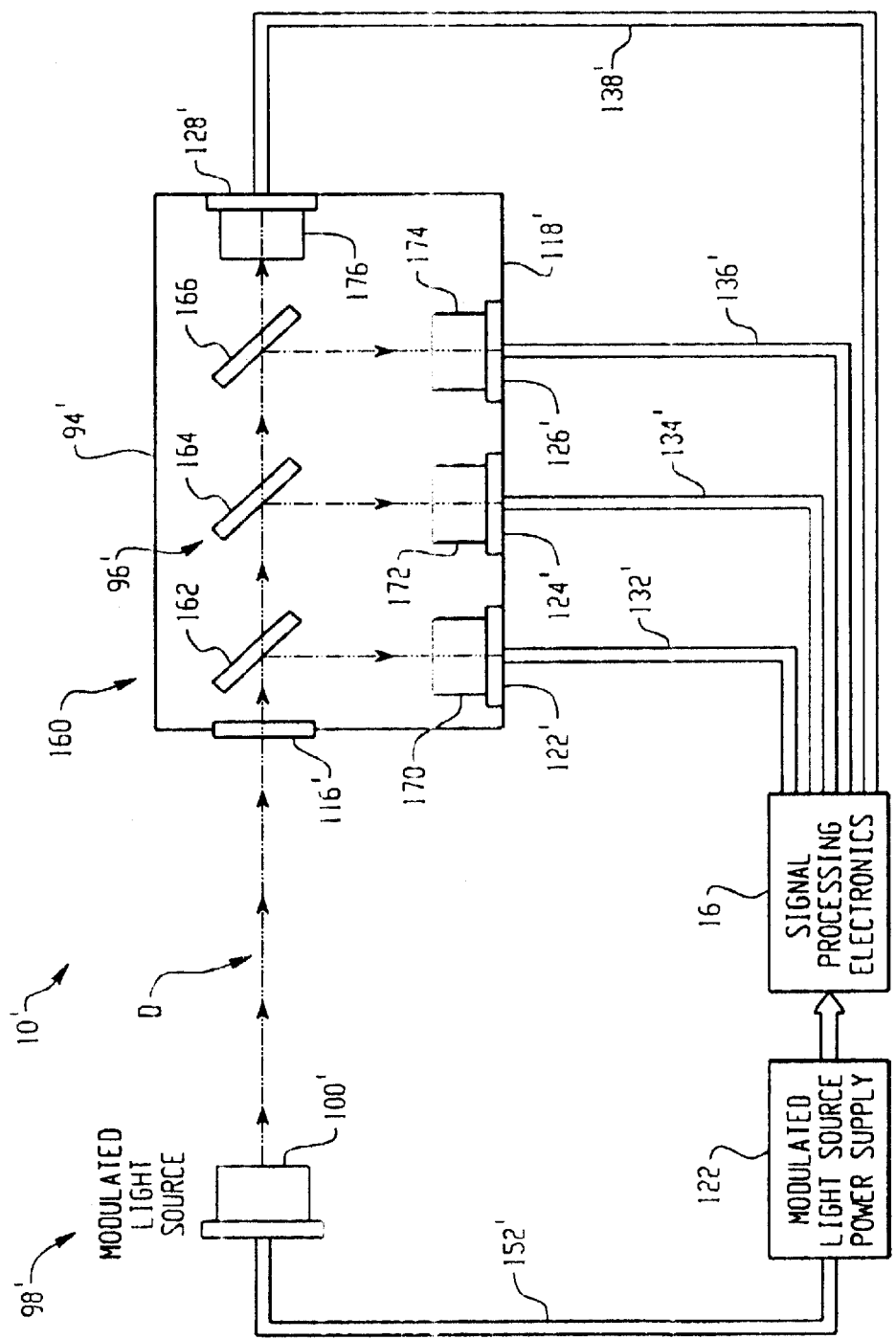
FIG. 7 is a schematic illustration of a second embodiment of the infrared sensor system of FIG. 1.

With reference now to FIG. 7, an alternative embodiment of a sensor probe 10' is shown. Similar components are identified with a prime (') while new components are given new numbers. The sensor probe includes a receiving portion 94', comprising a detection system 96', and a transmitting portion 98'. The transmitting portion includes a radiation source 100', such as an IR source, analogous to the modulated radiation source 100 of FIG. 2. The detection system and radiation source may be located within the chamber 12 or connected therewith by fiber optic cables, or the like. As for the embodiment of FIG. 2, the hollow body 102' acts both as a positioner for maintaining the alignment of the transmitting portion and receiving portion, and as a shield to prevent objects within the sterilization chamber 12 from obstructing the energy path D between the transmitting and receiving portions. The transmitting portion 98' preferably includes a casing (not shown) analogous to the casing 108. The receiving portion similarly includes a casing 118' and IR transmissive window 116' analogous to those of FIG. 2.

The detection system 96' includes a directing system 160, such as a number of beam splitters 162, 164, 166 (three are shown in FIG. 7), which is used to divide the light beam along two or more pathways (4 in the case of FIG. 7). The splitters are preferably zinc selenide or germanium windows which reflect a percentage of the light of all wavelengths and transmit the remainder of the light. The detection system includes a number of detectors 122', 124', 126', and 128', analogous to detectors 122, 124, 126, and 128, each one sensitive to a particular wavelength or wavelength range. The beam splitters thus divide the light, each one directing a portion of the light to a separate detector 122', 124', 126' respectively. The final detector 128' receives light which has passed uninterrupted through the three beam splitters.

Preferably, each detector includes an optical filter 170, 172, 174, 176 for selecting a selected wavelength range. The filters 170, 172, 174, 176 are analogous in function to the filter portions 120A, 120B, 120C, and 120D. For example, the filter 170 of the first detector 122' is selective for (i.e., transmits) the wavelength range $\lambda_1$, which corresponds to the broad hydrogen peroxide range L in FIG. 4 (e.g., from about 7.5–8.4 microns), to which the first detector is sensitive. The optical filter 172 of the second detector 124' is selective for the wavelength range $\lambda_2$, which corresponds to the water range (e.g., from about 5.2–7.2 microns), to which the second detector 124' is sensitive. The optical filter 174 of the third detector 126' is selective for the wavelength range $\lambda_3$, which corresponds to a range where neither hydrogen peroxide nor water vapor absorbs (e.g., from about 4.2–4.6 microns) to which the third detector 126' is sensitive. This detector may be used as a reference to determine the intensity of the transmitted light which is then used in calculation of absorbance values for the other detectors (absorbance is typically measured as the ratio of log intensity of detector/log intensity of reference detector). The fourth detector 128' is a second reference detector or sensitive to a narrow range $\lambda_4$ (e.g., from about 8.25–8.3 microns) as for the embodiment of FIG. 2. The casing 118' may be mounted within the chamber 12 or other part of the system 14. Or, it may be positioned outside the chamber, with the window 116' positioned in an opening in the chamber wall so as to receive the beam D. Or, the window may be connected with a light pipe, such as a fiber optic cable, which carries the beam D from the chamber to the window. Circuitry 132', 134', 136', 138' analogous to that of FIG. 2 connects the four detectors 122', 124', 126', and 128', respectively, with the controller 16.

It is to be understood that the sensor system 10 of the embodiment of FIGS. 2 and 7 may be simplified by omitting one or more of the components, such as one or more beam splitters (where present) and/or one or more of the detectors. For example, the water detector 124, 124' and its beam splitter 164, where present, may be eliminated, for example, if the concentration of water is determined by other methods. Either one of the high and low hydrogen peroxide detectors 136, 136', 142, 142' may be eliminated, for example, if the hydrogen peroxide concentrations to be detected fall within a fairly narrow range. Finally, the reference detector 140, 140' could be replaced by some other means of establishing reference intensities.

Having a filter 120A, 120B, 120C, 120D, 170, 172, 174, 176 associated with each detector 122, 122', 124, 124', 126, 126', 128, 128' reduces the sensitivity required of each detector. For example, each of the detectors 122', 124', 126', and 128' are optionally of identical configuration, the corresponding filter being used to determine the particular wavelengths detected.

Other methods of directing the beam to a plurality of detectors are also contemplated. For example, a prism may be used to split the beam D into light of different wavelength ranges, with the detectors positioned to receive a selected wavelength range.

More complex systems are also contemplated, for example, when there are more than two vapor components to be detected, additional detectors and optionally additional beam splitters may be employed and/or additional wavelength ranges measured to obtain data for these components. Or, it may be desirable to use more than two hydrogen peroxide detectors—e.g., a low, mid, and high level peroxide detector. The positions of the detectors may also be varied, for example, the high level detector may be switched with the low level detector.

As will also be appreciated, the width and/or wavelengths of the wavelength bands selected by the filters 120A, 120B, 120C, 120D, 170, 172, 174, 176 may be varied, depending on the concentration ranges likely to be encountered in the system being monitored and the particular chemical components under investigation.

The controller 16 receives signals from each of the detectors 122, 124, 126, 128, or 122', 124', 126', 128' and uses signal processing equipment to determine the hydrogen peroxide and/or water concentration of the vapor and correct for background noise. When two hydrogen peroxide detectors are used and the concentration of the hydrogen peroxide is relatively low, for example, when the absorption signals measured by the high level peroxide detector 128, 128' are below a predetermined level (or outside its range), the controller ignores the signals from the high level detector and uses the signals from the low level detector 122, 122'. Conversely, when the concentration of the hydrogen peroxide is relatively high, i.e., above a preselected minimum concentration, and the absorption signals measured by the low level peroxide detector 122, 122' are above a predetermined level (or outside its range) the controller ignores the signals from the low level detector and uses the signals from the high level detector.

By use of two or more detectors, each at a different wavelength or wavelength range, a wide range of hydrogen peroxide concentrations can be sensed without the need for complex converters.

The modulated light source power supply 100, 100' is coupled to the signal processing electronics of the embedded controller 140 or the controller 16 to inform the controller of the pulse rate of the modulated signal, allowing the electronics to accommodate for the pulses.

Figure 8:
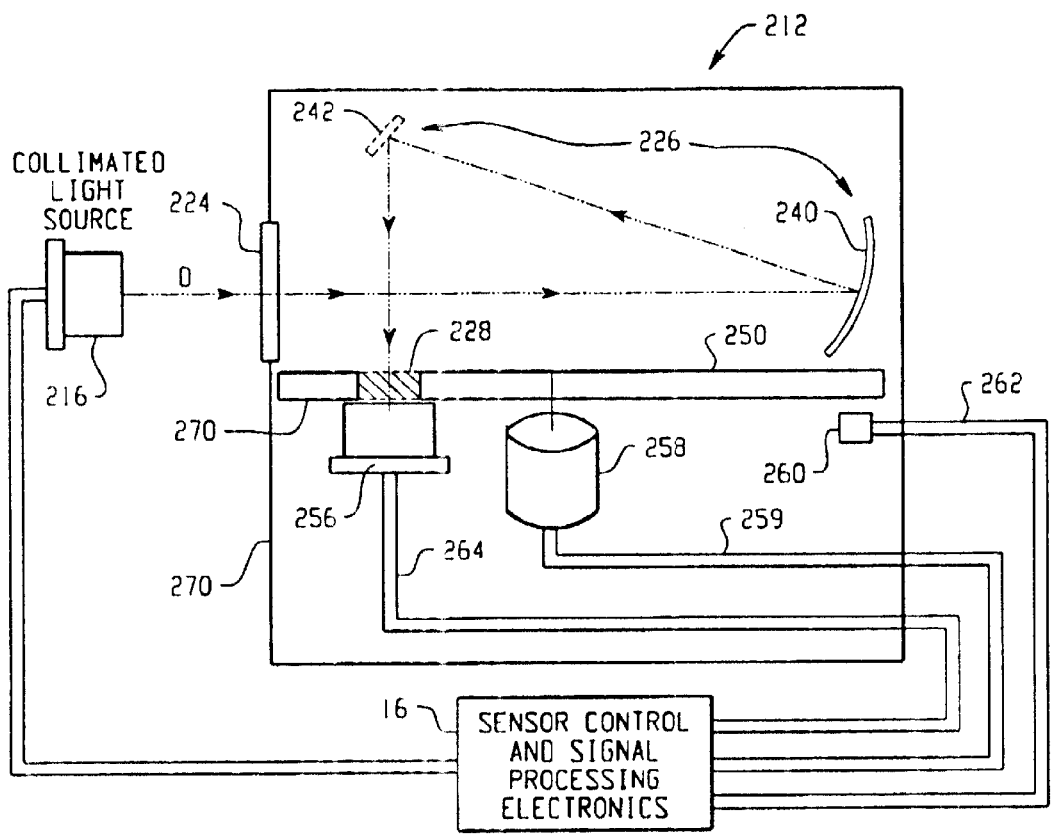
FIG. 8 is a schematic illustration of a third embodiment of the infrared sensor system of FIG. 1.
Figure 9:
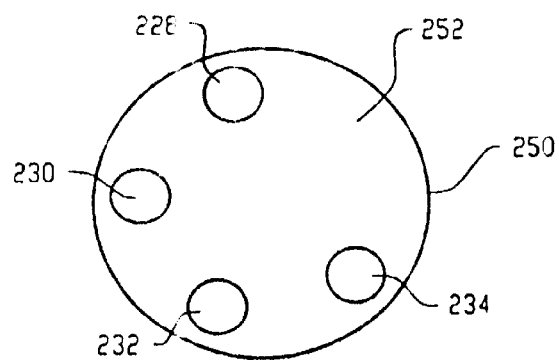
FIG. 9 is a top plan view of the filter wheel of FIG. 8.

With reference now to FIG. 8, a third embodiment of a detection system 212 is shown. In this embodiment, a beam of light D analogous to that of the first embodiment is emitted by a collimated light source 216. The beam of light travels through the vapor to be detected and enters a window 224 of the detector portion. The light is directed by a direction system 226 on to one of a selection of filters 228, 230, 232, 234 (four are shown in FIG. 9). As shown in FIG. 8, the direction system includes a first reflective surface 240, such as a concave focusing mirror, which focusses the beam of light onto a second reflective surface or bending mirror 242. The bending mirror reflects the light on to the selected filter. Other systems for directing the light on to the filter are also contemplated.

Optionally, at least a first of the filters 228 is selective for (i.e., transmits) light within block H, as described above, and a second filter 230 is selective for light in block L, for detection of hydrogen peroxide at high concentrations and at low concentrations, respectively. A third (optional) filter 232 provides a reference channel, by selecting for a region of the spectrum where no species absorb, for detecting background levels. A fourth filter 234 is selective for water alone. Alternatively, as for the embodiment of FIG. 7, one of the filters 230 acts as a second reference filter. As will be appreciated from the discussion of FIG. 7, one or more of these filters may be omitted, provided that at least one filter is provided for detection of hydrogen peroxide or other component of interest.

As shown in FIG. 9, the filters 228, 230, 232, 234 are circumferentially spaced around a rotating filter wheel 250. A fifth circumferentially spaced region 252 on the wheel is preferably left filled to allow measurement of the detector background signal. The wheel 250 is rotatable such that the filters are sequentially positioned in front of a detector 256. A motor 258, connected with the filter wheel, rotates the wheel during detection. The motor is under the control of or has its rotational speed monitored by the microprocessor 16 via a connector 259. An optical pickup 260 detects the position of the wheel and feeds the information to the signal processing electronics of the microprocessor 16 via a connector 262. Another connector 264, which may include circuitry analogous to circuitry 132 of FIG. 6, feeds information from the detector 256 to the microprocessor 16. From this information, the signal processing electronics can correlate the signal with the filter being used at any particular time. Alternatively, the optical pickup 260 may be eliminated and the speed of the motor 258 used to determine the position of the filters 228, 230, 232, 234. The filter wheel, mirrors, detector, motor, and optical pickup are preferably housed within a casing 270.

While a filter wheel 250 is a convenient means for changing the filter 228, 230, 232, 234, other methods of selectively interposing the filters between the beam D and the detector 256 are also contemplated. For example, the filters may remain stationary while the detector is moved. Or, the filters may be manually moved into position, for example, by operation of a switch (not shown).

As will be appreciated, the detector 256 in this embodiment is sensitive to a wider range of wavelengths than may be needed for each individual detector 122, 124, 126, 128 of the first and second embodiments. The detector 256 encompasses each of the ranges to be studied, and thus, for hydrogen peroxide/water vapor mixtures, may be selective to a wavelength range of from about 5 to about 8.5 microns.

In this embodiment, the light source 216 need not provide a modulated (pulsed) beam, since the filter wheel 250 provides this function.

It will be appreciated that the bending and focussing mirrors 242, 240 of this embodiment are optionally used in combination with one or more of the detectors 122, 124, 126, 128 of FIGS. 2 and 7.

Figure 10:
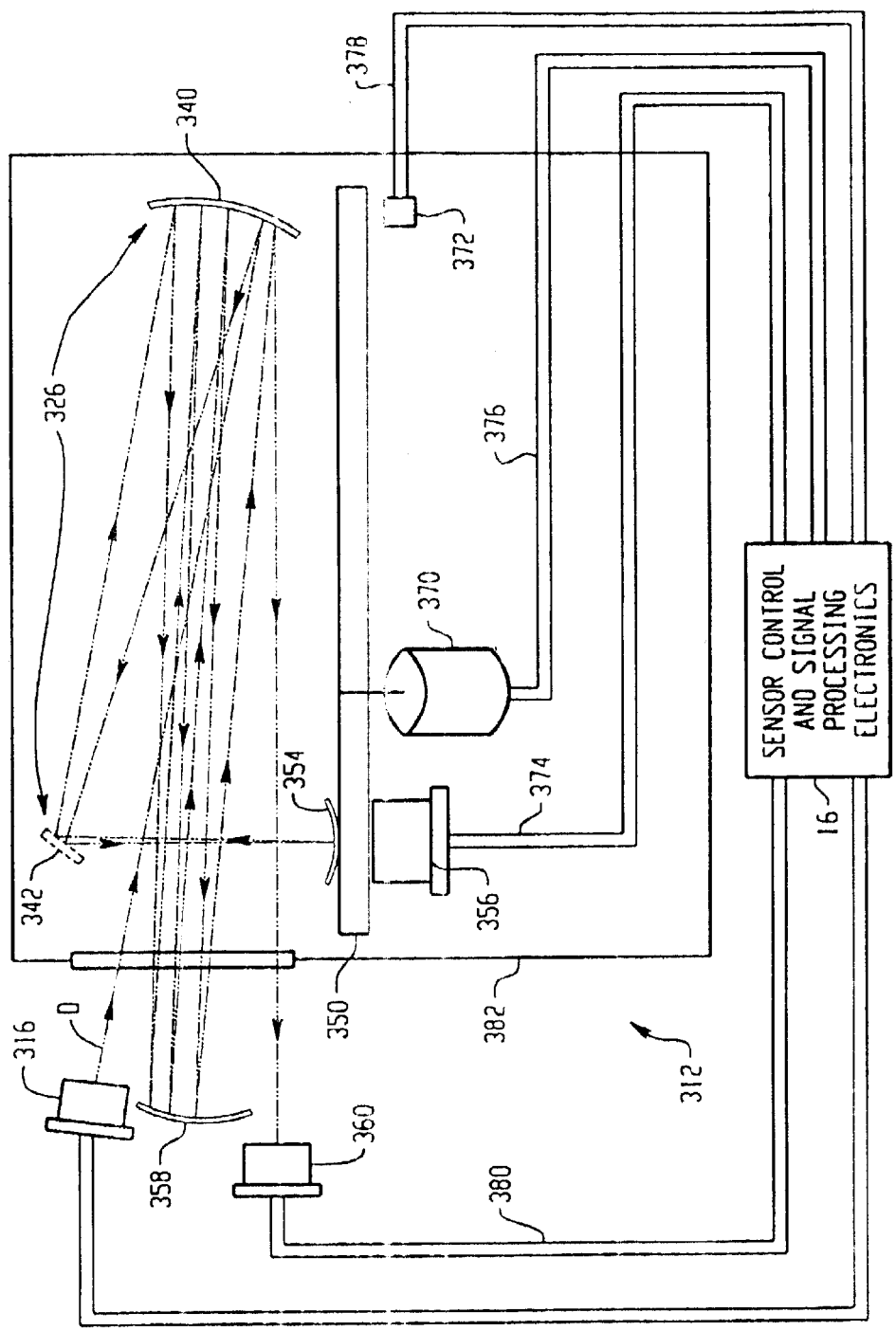
FIG. 10 is a schematic illustration of a fourth embodiment of the infrared sensor system of FIG. 1.
Figure 11:
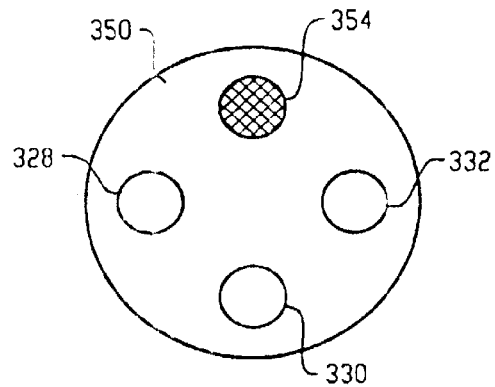
FIG. 11 is a top plan view of the filter wheel of FIG. 10.

A fourth embodiment of a detection system 312 is shown in FIGS. 10 and 11. In this embodiment, the system is similar to the third embodiment, in that a collimated light source 316 (which need not be modulated) directs a beam of light D through the vapor and into the window 324 of a detection system 312. The light is directed by a directing system 326 onto one of a group of filters 328, 330, 332. As with the third embodiment, the directing system includes a focussing mirror 340 which focusses the beam on to a bending mirror 342. The light is then reflected on to a rotating filter wheel 350 (FIG. 11).

The filter wheel 350 is similar to that of the third embodiment, but has four circumferentially spaced positions instead of five. The first, second, and third positions are occupied by filters 328, 330, 332, similar to filters 228, 232, and 234 of the third embodiment. Filter 328 is selective for high concentration hydrogen peroxide by selecting light within block H, as described above, or acts as a reference channel. Filter 330 provides a reference channel, by selecting for a region of the spectrum where no species absorb, for detecting background levels, and filter 332 is selective for water alone.

The fourth position is occupied by a reflective surface 354, such as a concave mirror, which, when positioned between the beam and a first detector 356, prevents the light from entering the detector 356. Instead, the mirror reflects the light back up to the directing system, although along a slightly different path from the incoming path, so that the light first strikes the bending mirror 342 then is reflected several times through the vapor between the focussing mirror 340 and a third mirror 358 before striking a second detector 360. The second detector is sensitive to wavelengths in the low level range L for detection of low concentrations of hydrogen peroxide. The multiple bounces and the resultant increased path length through the vapor increases the absorbance being detected and thus allows for greater sensitivity to low concentrations of hydrogen peroxide. This embodiment eliminates the need for a narrow band path filter, as used in the third embodiment for detecting high levels of hydrogen peroxide.

As with the third embodiment, a motor 370 rotates the filter wheel 350 and an optical pickup detects 372 the rotational position of the filters 328, 330, 332 and reflective surface 354. The detectors 356, 360 motor 370, and optical pickup 372 are electrically connected with the microprocessor by connectors 374, 376, 378, 380, which may include circuitry analogous to circuitry 132, 134, 146, 138 of FIG. 6. As with the other embodiments, a casing 382 protects the directing system 326, detector 356, filter wheel 350, motor 370, and optical pickup 372. The second detector 360 and third mirror 358 are preferably positioned adjacent the collimated light source 316, such as in a casing (not shown) for the light source 316, or at another suitable position for causing the beam to pass multiple times through the vapor to allow for much higher absorption of the light by the hydrogen peroxide than would occur in a single pass through the vapor.

It will be appreciated that a path length extension system similar to that of FIG. 10 may be incorporated into the detection systems of FIGS. 2 and 7. Specifically, a pair of opposed mirrors analogous to mirrors 340 and 358 could be used to increase the path through the vapor, at least for the hydrogen peroxide detector 122, 122', particularly when low levels of hydrogen peroxide are to be detected.

In a preferred embodiment, the microprocessor 16 provides a digital readout of the concentration of hydrogen peroxide vapor and a digital or analog output signal to the microprocessor-controller 30, shown in FIG. 1, or other process control device. In an alternative embodiment, the microprocessor 16 provides an analog signal output which allows its own controller to control directly the operation of the sterilizer system. As an alternative, microprocessor 16 may provide a digital output, which is fed into a converter which may be included in a personal computer (PC), which converts the signal to an analog output for transmission to the controller 30. In microprocessor-controller 30, the signal is integrated with other operational signals, such as temperature, pressure and relative humidity, obtained directly from devices in the chamber 12 by way of the connectors 86, 88. The output from the microprocessor-controller 30 is preferably a plurality of analog signals, to control directly the operation of the various components of the sterilizer system. For example, as shown in FIG. 1, signals from the microprocessor-controller 30 control the temperature in the chamber via connector 84 to the heater 82, and/or control the pressure in the chamber via the connector 78 to the valve 74. As shown in FIG. 1, signals from the microprocessor-controller 30 control operation of the dryer 62 via a connector 64, and may control flow of carrier gas into the system via the connector 81 to the valve 80. Finally, as shown in FIG. 1, microprocessor-controller 30 may control whether the system is operated as a flow-through or deep vacuum system through its connection to valve 74 via connector 76 and valve 54 via connector 56.

The optimum hydrogen peroxide vapor concentration and/or percent saturation are functions of several different variable conditions in the sterilization process. In a preferred embodiment, the microprocessor portion of the microprocessor-controller 30 is programmed to calculate the optimum hydrogen peroxide concentration and/or percent saturation based on the variable conditions under which the sterilization apparatus is being operated.

The most preferred system for monitoring and controlling the sterilant vapor concentration is also capable of monitoring and controlling other relevant parameters, including temperature, pressure, humidity and relative humidity. Accordingly, the system preferably includes either a means of directly measuring the water content (humidity) in the sterilization chamber either by use of the sensor probe 10, or by a separate humidity sensor, particularly in deep vacuum and closed flow-through systems, or of estimating the water content based on the relative humidity of air entering the system in an open flow-through system. The values obtained for water content are most preferably entered into the microprocessor-controller in order to allow control of relevant system parameters, according to the programming of the microprocessor. The water content of the circulating carrier gas may be controlled in flow-through systems so equipped by use of a dryer or by controlling the proportion of water in the hydrogen peroxide solution being fed to the vaporizers. In deep vacuum systems, the water content, as discussed above, is a function of the pressure, so by maintaining a very low pressure, the water content may be kept within acceptable limits.

The IR sensor probe 10 or other sensor probe used with the system of the present invention is calibrated to known concentrations of hydrogen peroxide vapor (or other vapor component to be measured). Such calibration using the IR sensor probe 10 is described below for a flow-through hydrogen peroxide vapor sterilization apparatus. Calibration of a deep vacuum hydrogen peroxide vapor apparatus would proceed in generally the same manner as the flow-through system.

In one embodiment, the sensor probe 10 is calibrated within the chamber 12. The probe is bathed in a flow of carrier gas and a first concentration of hydrogen peroxide vapor passing through the sterilization chamber 12. Preferably, the temperature and pressure of the calibration procedure is close to that of the actual sterilization process. Additionally, in order to maintain a reasonably constant level of hydrogen peroxide vapor in the chamber 12, the chamber 12 has no load during the calibration operation.

The sensor system 1 is operated to determine the absorbance at the selected wavelength(s) for the first hydrogen peroxide vapor concentration. Through an opening (not shown) in or within the sterilization chamber 12, one or more samples of the circulating multi-component vapor are collected and trapped by suitable means for each hydrogen peroxide vapor concentration to be determined for the standard curve. These samples are analyzed by conventional means, such as chemical titration, to establish a calibration curve or extinction coefficient (absorbance value per unit concentration of hydrogen peroxide).

Figure 12:
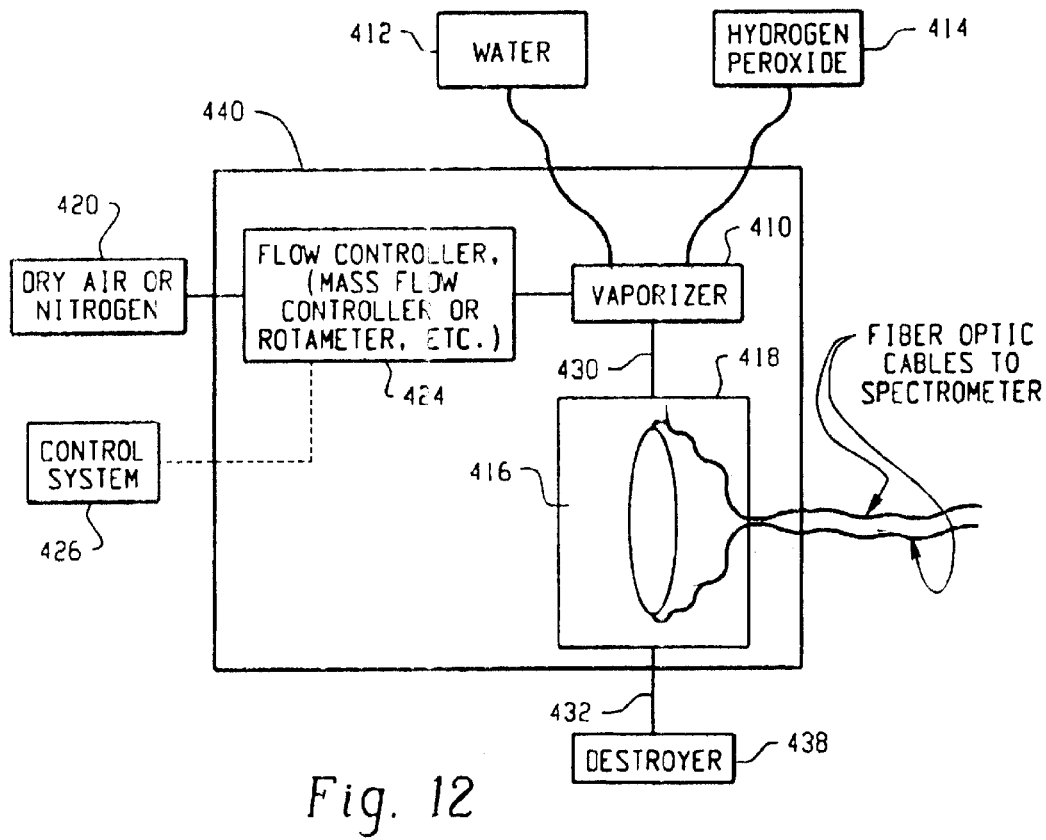
FIG. 12 is a schematic illustration of a calibration system according to the present invention; and, FIG. 13 is a perspective view of the probe of FIG. 1.

In another method, calibration of the probe 10 is carried out by a mass balance method, either in the sterilization chamber 12, or, more preferably, it may be calibrated in a dedicated apparatus, as shown in FIG. 12, to ensure accurate results. In this embodiment, a system is set up which allows the probe to be completely immersed in a flow of a carrier gas, such as dry air, nitrogen, or other dry gas. A vaporizer 410 is used to introduce small, known, variable flows of water and hydrogen peroxide into the incoming carrier gas. This allows the incoming gas to be loaded with known concentrations of hydrogen peroxide plus water vapor (for example, by weighing a source vessel 412 of water or a source vessel 414 of a hydrogen peroxide and water mixture at intervals on a balance). The probe is positioned within a chamber 416 defined by a housing 418 or other vessel, through which the mixture of carrier gas and vapor is flowed. The exact concentration of the hydrogen peroxide in the chamber 416 is not known from the injection rates, however, since some of the hydrogen peroxide vapor may have decomposed to water.

Dry air or other carrier gas from a source 420 of carrier gas is passed via a flow controller 424, such as a mass flow controller or rotameter, to the vaporizer 410. The flow controller provides a control system 426 with information from which the amount (e.g., weight) or proportion of carrier gas in the flowing vapor/carrier gas mixture can be determined. The sources of water and hydrogen peroxide solution (s) 412, 414 are fluidly connected with the vaporizer for supplying these liquids to the injectors of the vaporizer. The carrier gas and vapor mixture is carried into the chamber 416 via an inlet 430 and flows over the probe 10. An outlet 432 carries the flowing mixture out of the chamber to a destroyer 434. Preferably, the flow controller 424, vaporizer 410, and probe chamber 416 are enclosed in a thermostatically controlled outer chamber 440 to minimize the effects of environmental temperature changes and to keep the probe chamber and vapor at an even temperature. Alternatively or additionally, the probe chamber 416 may have its own heater.

A first step is to collect spectral data from a series of water concentrations in the carrier gas, with no hydrogen peroxide present. Depending on which embodiment of the probe is used, the appropriate water detector, 124, 124', 256, 356 detects the water and provides a signal to the controller 16. Using this data, the extinction coefficients for water at the wavelengths to be monitored by the probe are determined.

Then, hydrogen peroxide/water mixtures are introduced to the probe chamber 416 and absorbance data are collected over a range of injection rates at least two wavelengths or wavelength ranges, one where hydrogen peroxide does not absorb light (e.g., around 3.5–4 microns), the other at a wavelength where at least hydrogen peroxide absorbs light (e.g., about 7.5–8.4 microns). The concentration of hydrogen peroxide in the hydrogen peroxide solutions tested are determined, immediately prior to the calibration test, for example by an assay technique, such as titration (e.g., the concentration traced to N.I.S.T. primary standard sodium oxalate) so that the amount of hydrogen peroxide being injected into the vaporizers is known.

The amount of water injected, either as water, or as solvent for hydrogen peroxide is determined from the flow rate of carrier gas and the injection rate of the water or water/hydrogen peroxide mixture. The absorbances of water are found at one or more wavelengths where hydrogen peroxide does not absorb light (e.g., about 5.2–7.2 microns), allowing a plot of water vapor concentration vs absorbance to be drawn. From these calibration models, the amount of water present in the hydrogen peroxide and water vapor mixture in the chamber can be determined—this amount will differ from the amount of water injected due to the conversion of some hydrogen peroxide to water. Since one mole of hydrogen peroxide yields one mole of water on conversion, the amount of hydrogen peroxide which has been converted to water can be determined. This allows the amount of hydrogen peroxide in the vapor which has not decomposed to be calculated by subtracting the amount of hydrogen peroxide converted to water vapor from the amount of hydrogen peroxide being injected. Using this information, the extinction coefficients for the hydrogen peroxide can be determined. This information can then be used in the calibration data set for the probe 10.

Although the preferred embodiment of the present invention comprises hydrogen peroxide vapor as the sterilant vapor and electromagnetic radiation having wavelengths in the mid-infrared region as the radiation for detecting the sterilant concentration, other wavelengths of electromagnetic radiation may be useable for this or other sterilants. Sterilants other than hydrogen peroxide can be used with the system and method of the present invention. The selection of the proper wavelengths depends on electromagnetic properties of the sterilant vapor and any other vapors present in a multi-component vapor.

Preferably the wavelengths chosen allow the concentration of one component to be determined by selecting a wavelength or wavelength range where other species in the vapor do not contribute (or contribute an insignificant amount) to the total absorbance by the vapor. Alternatively, where the absorbencies overlap, a subtraction procedure may be used, provided that the overlapping component absorbs in at least two regions of the spectrum. Using data manipulation, the contribution of the overlapping component may be subtracted out. Or, a chemometric method may be employed to determine concentrations from two or more overlapping peaks. More preferably, a wavelength of absorbance unique to the sterilant or other vapor of interest is available and not interfered with by other components of the multi-component vapor.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. A method of microbial or chemical decontamination comprising:

exposing an item to be microbially or chemically decontaminated to a multi-component vapor which includes a gaseous oxidant and a second vapor component; and detecting the gaseous oxidant in the multi-component vapor including:

directing light through the multi-component vapor, the directed light including light of at least a first wavelength range where the gaseous oxidant absorbs but at which the second vapor component does not significantly absorb, the first wavelength range including one or more wavelengths between about 7500 and 8400 nanometers, detecting the absorbance of light which has passed through the vapor in the first wavelength range, and determining the concentration of the gaseous oxidant in the multi-component vapor from the detected absorbance.

2. The method of claim 1, wherein the gaseous oxidant includes hydrogen peroxide.

3. The method of claim 1, wherein the second vapor component includes water and the directed light further includes light of a second wavelength range, the second wavelength range being spaced from the first wavelength range, where water absorbs and the gaseous oxidant does not significantly absorb, the step of detecting the absorbance of light further including:

detecting the absorbance of light in the second wavelength range; and determining the concentration of water in the multi-component vapor from the detected absorbance in the second wavelength range.

4. A method of microbial or chemical decontamination comprising:

exposing an item to be microbially or chemically decontaminated to a multi-component vapor which includes a gaseous oxidant and water; and detecting the gaseous oxidant and water in the multi-component vapor including:

directing light through the multi-component vapor, the directed light including light of a first wavelength range and a second wavelength range, the first wavelength range being where the gaseous oxidant absorbs but at which water does not significantly absorb, the first wavelength range including one or more wavelengths between about 7500 and 8400 nanometers, the second wavelength range being spaced from the first wavelength range, where water absorbs and the gaseous oxidant does not significantly absorb, the second wavelength range being in the range of from about 5200 nanometers to about 7200 nanometers, detecting the absorbance of light which has passed through the vapor in the first wavelength range, and determining the concentration of the gaseous oxidant in the multi-component vapor from the detected absorbance in the first wavelength range, detecting the absorbance of light in the second wavelength range, and determining the concentration of water in the multi-component vapor from the detected absorbance in the second wavelength range.

5. The method of claim 1, wherein the directed light further includes light of a third wavelength range, the third wavelength range being spaced from the first and second wavelengths, where both the second vapor component and the gaseous oxidant do not significantly absorb, the method further including:

detecting the absorbance of light in the third wavelength range; and determining a background absorption value from the detected absorbance detecting the absorbance of light in the third wavelength range.

6. The method of claim 1, further including:

in response to the determined concentration of the gaseous oxidant being outside a preselected concentration range, controlling at least one of:

a length of time to which the item is exposed to the vapor;

a pressure of the vapor;

a temperature of the vapor; and a rate at which the gaseous oxidant is added to the vapor;

to maintain selected decontamination conditions whereby the item is effectively decontaminated.

7. The method of claim 6, further including monitoring at least one of:

the pressure of the vapor;

the temperature of the vapor; and the relative humidity of the vapor.

8. The method of claim 6, wherein the gaseous oxidant is hydrogen peroxide and the step of controlling the rate at which hydrogen peroxide is added to the vapor includes controlling the rate at which liquid hydrogen peroxide is admitted to a vaporizer which generates the multi-component vapor.

9. The method of claim 8, wherein the step of controlling includes maintaining the concentration of hydrogen peroxide in the vapor below its saturation point, whereby condensation of vapor on the item is minimized.

10. The method of claim 1, further including:

passing a first portion of the light which has passed through the vapor through a first filter which is selective for light in the first wavelength range; and detecting the absorption of light which has been filtered by the first filter with a first detector.

11. The method of claim 10, further including:

passing a second portion of the light which has passed through the vapor through a second filter which is selective for light in a second wavelength range at which water absorbs, but at which hydrogen peroxide does not significantly absorb; and detecting the absorption of light which has been filtered by the second filter with a detector.

12. The method of claim 11, where the detector which detects the absorption of light which has been filtered by the second filter is the first detector and the method further includes:

moving the first and second filters such that the first detector sequentially receives light which has passed through the first filter and light which has passed through the second filter.

13. The method of claim 1, wherein the step of detecting includes:

detecting the absorbance of light which has passed through the vapor over a first portion of the first wavelength range when the gaseous oxidant concentration is above a threshold value, and detecting the absorbance of light which has passed through the vapor over a second portion of the first wavelength range when the gaseous oxidant concentration is below the threshold value, the absorbance of gaseous oxidant in the second portion of the first wavelength range being higher than the absorbance of gaseous oxidant in the first portion of the first wavelength range.

14. The method of claim 13, wherein the gaseous oxidant is hydrogen peroxide and at least one of the following conditions applies:

the first portion of the first wavelength range includes wavelengths of no less than about 8200 nm; and the first and second portions of the first wavelength range are overlapping.

15. The method of claim 1, wherein the method further includes:

providing a modulated beam of the directed light; and wherein the step of directing light includes:

directing the modulated beam of light through the multi-component vapor.

16. The method of claim 15, wherein the step of directing the light through the multi-component vapor further includes:

reflecting the light such that it passes back and forth through the multi-component vapor a plurality of times.

17. A method of microbial or chemical decontamination comprising:

exposing an item to be microbially or chemically decontaminated to a multi-component vapor which includes a gaseous oxidant and a second vapor component;

directing light through a sensor system including a transmitting portion which directs the light through the multi-component vapor and a receiving portion which receives light which has passed through the multi-component vapor, louvers being provided intermediate the transmitting portion and the receiving portion which permit the vapor to pass through the directed light but which inhibit stray radiation from being detected, the directed light including light of at least a first wavelength range where the gaseous oxidant absorbs but at which second vapor component does not significantly absorb, the first wavelength range including one or more wavelengths between about 7500 and 8400 nanometers;

detecting the absorbance of light which has passed through the vapor in the first wavelength range; and determining the concentration of the gaseous oxidant in the multi-component vapor from the detected absorbance.

18. A method for determining the concentration of hydrogen peroxide and water in a multi-component vapor, the method including:

directing light through the multi-component vapor, the light including wavelengths in a first wavelength range of the mid infrared spectrum at which hydrogen peroxide absorbs but at which water does not significantly absorb and wavelengths in a second wavelength range of the mid infrared spectrum at which water absorbs but at which hydrogen peroxide does not significantly absorb, the mid infrared spectrum being from 2000–10,000 nanometers;

detecting light which has passed through the multi-component vapor in the first wavelength range;

separately detecting light which has passed through the multi-component vapor in the second wavelength range; and determining concentrations of water and hydrogen peroxide in the multi-component vapor from detected light in the first and second wavelength ranges.

19. A decontamination system comprising:

a chamber which receives items to be microbially decontaminated;

a source of a gaseous sterilant which supplies the gaseous sterilant to the chamber;

a sensor system including:

a transmitting portion which directs light through the gaseous sterilant; and a receiving portion which receives light which has passed through the gaseous sterilant, the receiving portion including:

a first detector positioned to receive light which has passed through the gaseous sterilant, the first detector detecting light in a wavelength range of the mid-infrared spectrum at which a first component of the gaseous sterilant absorbs, the mid-infrared spectrum being from 2000–10,000 nanometers; and a control system which controls conditions within the chamber in response to a signal indicative of the light detected by the first detector.

20. The system of claim 19, wherein the receiving portion further includes:

a filter positioned to filter light to be received by the first detector.

21. The system of claim 19, further including:

a second detector which detects light in a second wavelength range spaced from the first wavelength range at which a second component of the sterilant absorbs but at which the first component does not substantially absorb.

22. A decontamination system comprising:

a chamber which receives items to be microbially decontaminated;

a source of a gaseous sterilant which supplies the gaseous sterilant to the chamber, the sterilant including a mixture of water vapor and vapor hydrogen peroxide;

a sensor system including:

a transmitting portion which directs light through the gaseous sterilant; and a receiving portion which receives light which has passed through the gaseous sterilant, the receiving portion including:

a first detector positioned to receive light which has passed through the gaseous sterilant, the first detector detecting light in a wavelength range of from about 7500 to 8400 nm at which a first component of the gaseous sterilant absorbs, a second detector positioned to receive light which has passed through the gaseous sterilant, the second detector detecting light in a wavelength range of from about 5200 to 7200 nm at which a second component of the gaseous sterilant absorbs and the first component does not absorb; and a control system which controls conditions within the chamber in response to a signal indicative of the light detected by the first detector.

23. A decontamination system comprising: a chamber which receives items to be microbially decontaminated;
   a source of a gaseous sterilant which supplies the gaseous sterilant to the chamber;
   a sensor system including:
      a transmitting portion which directs light through the gaseous sterilant;
      a receiving portion which receives light which has passed through the gaseous sterilant, the receiving portion including:
         a first detector positioned to receive light which has passed through the gaseous sterilant, the first detector detecting light in a wavelength range of the mid-infrared spectrum at which a first component of the gaseous sterilant absorbs, and
      an elongated polygonally cross sectional, apertured tube connected with the transmitting and receiving portions to maintain the transmitting and receiving portions in a fixed relationship; and
   a control system which controls conditions within the chamber in response to a signal indicative of the light detected by the first detector.

24. The system of claim 23, wherein the apertured tube includes louvers adjacent the apertures which inhibit stray radiation from entering the receiving portion.

25. The system of claim 23, wherein the detector is displaced from the apertured tube to shield the detector from stray light.

* * * * *